(12) United States Patent
Lin et al.

(10) Patent No.: US 10,048,220 B2
(45) Date of Patent: Aug. 14, 2018

(54) BIOSENSOR FIELD EFFECT TRANSISTOR HAVING SPECIFIC WELL STRUCTURE AND METHOD OF FORMING THE SAME

(71) Applicant: TAIWAN SEMICONDUCTOR MANUFACTURING COMPANY LTD., Hsinchu (TW)

(72) Inventors: Shih-Wei Lin, Taipei (TW);
Chang-Ming Wu, New Taipei (TW);
Lee-Chuan Tseng, New Taipei (TW);
Shih-Chang Liu, Kaohsiung County (TW)

(73) Assignee: TAIWAN SEMICONDUCTOR MANUFACTURING COMPANY LTD., Hsinchu (TW)

(*) Notice: Subject to any disclaimer, the term of this patent is extended or adjusted under 35 U.S.C. 154(b) by 0 days.

(21) Appl. No.: 14/878,999

(22) Filed: Oct. 8, 2015

(65) Prior Publication Data

US 2017/0102356 A1  Apr. 13, 2017

(51) Int. Cl.
*G01N 27/414* (2006.01)

(52) U.S. Cl.
CPC .................. *G01N 27/4145* (2013.01)

(58) Field of Classification Search
CPC .................................................. G01N 27/4145
See application file for complete search history.

(56) References Cited

U.S. PATENT DOCUMENTS

| 8,841,217 B1* | 9/2014 | Fife | G01N 27/414 257/288 |
|---|---|---|---|
| 2013/0105868 A1* | 5/2013 | Kalnitsky | G01N 27/414 257/288 |
| 2013/0189790 A1* | 7/2013 | Li | B01L 3/5027 436/94 |
| 2014/0061729 A1* | 3/2014 | Koo | G01N 27/4148 257/253 |
| 2014/0272719 A1* | 9/2014 | Liu | G03F 7/20 430/322 |
| 2017/0059517 A1* | 3/2017 | Bustillo | H01L 29/42324 |

FOREIGN PATENT DOCUMENTS

GB  2508582 A * 6/2014 ......... G01N 27/4148

OTHER PUBLICATIONS

Definition of "vertical" avialable at https://www.collinsdictionary.com/us/dictionary/english/vertical.*

* cited by examiner

*Primary Examiner* — Erik Kielin
(74) *Attorney, Agent, or Firm* — WPAT, P.C., Intellectual Property Attorneys; Anthony King

(57) ABSTRACT

A semiconductor structure and a method for forming the same are provided. The semiconductor structure comprises a substrate, a gate structure over a first surface of the substrate, and a source region and a drain region in the substrate adjacent to the gate structure. The semiconductor structure further comprises a channel region interposing the source and drain regions and underlying the gate structure. The semiconductor structure further comprises a first layer over a second surface of the substrate opposite to the first surface, and a second layer over the first layer. The semiconductor structure further comprises a sensing film over the channel region and at least a portion of the first and second layers, and a well over the sensing film and cutting off the first layer and the second layer.

18 Claims, 22 Drawing Sheets

BIOSENSOR FIELD EFFECT TRANSISTOR HAVING SPECIFIC WELL STRUCTURE AND METHOD OF FORMING THE SAME

FIELD

The present disclosure relates generally to a semiconductor structure and more particularly to a semiconductor structure of a biosensor.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BioFETs (biologically sensitive field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, integration of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
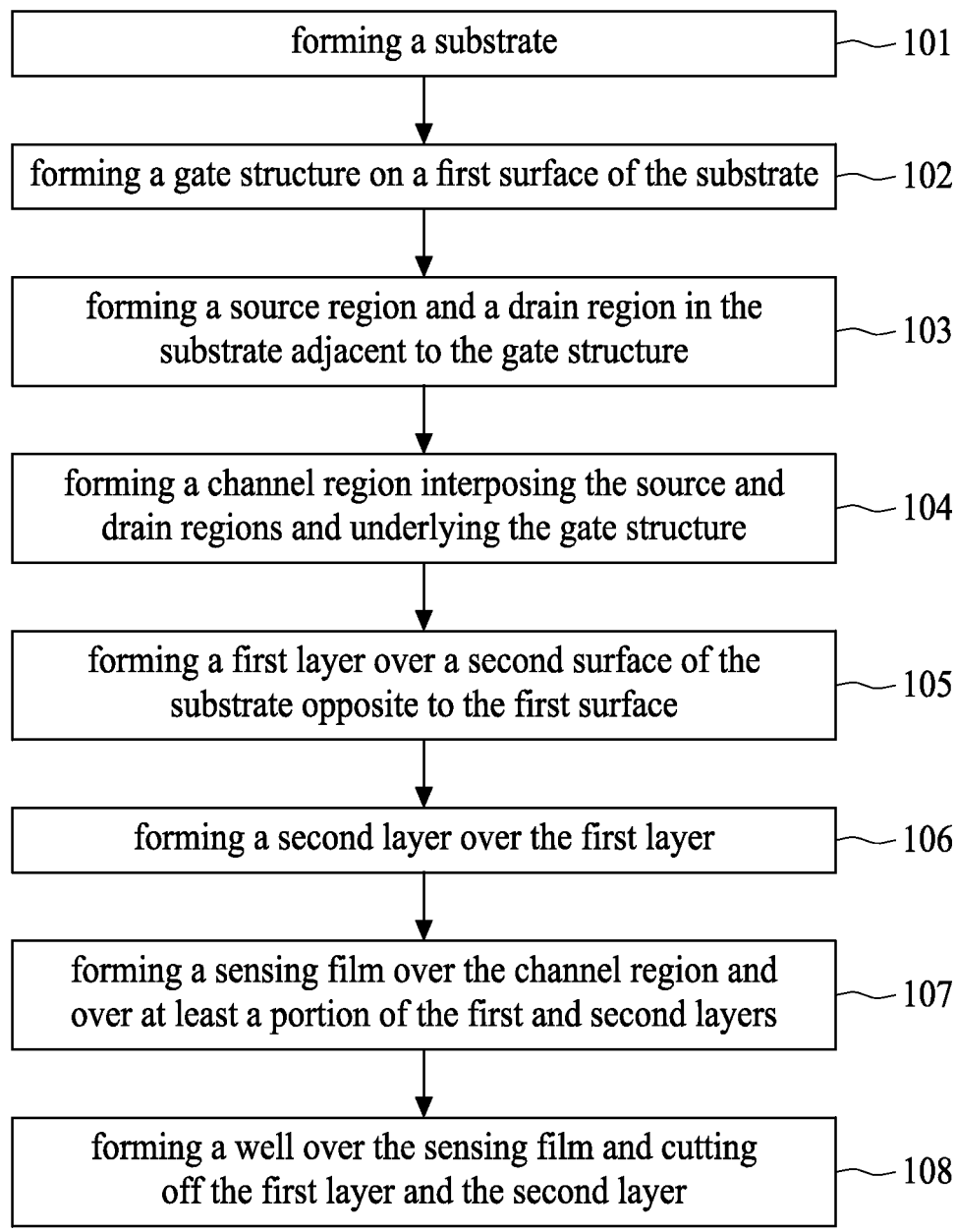
FIG. 1 is a flow chart illustrating a method of forming a semiconductor structure in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In a BioFET, the gate of a metal-oxide-semiconductor field-effect transistor (MOSFET), which controls the conductance of the semiconductor between the BioFET's source and drain contacts, is replaced by a bio- or biochemical-compatible layer or a biofunctionalized layer of immobilized probe molecules that act as surface receptors. Essentially, a BioFET is a field-effect biosensor with a semiconductor transducer. A decided advantage of BioFETs is the prospect of label-free operation. Specifically, BioFETs can avoid costly and time-consuming labeling operations such as the labeling of an analyte with, for instance, fluorescent or radioactive probes.

A typical detection mechanism for BioFETs is the conductance modulation of the transducer due to the binding of a target biomolecule or bio-entity to a sensing surface or a receptor molecule immobilized on the sensing surface of the BioFET. When the target biomolecule or bio-entity is bonded to the sensing surface or the immobilized receptor, the drain current of the BioFET is varied by the potential from the sensing surface. This change in the drain current can be measured and the bonding of the receptor and the target biomolecule or bio-entity can be identified. A great variety of biomolecules and bio-entities may be used to functionalize the sensing surface of the BioFET such as ions, enzymes, antibodies, ligands, receptors, peptides, oligonucleotides, cells of organs, organisms and pieces of organic tissue. For instance, to detect ssDNA (single-stranded deoxyribonucleic acid), the sensing surface of the BioFET may be functionalized with immobilized complementary ssDNA strands. Also, to detect various proteins such as tumor markers, the sensing surface of the BioFET may be functionalized with monoclonal antibodies.

A well is formed in a semiconductor structure of a BioFET. The well is used for receiving the target biomolecule or bio-entity. Because forming the well may comprise oxide thinning processes, dry etching processes and wet etching processes, dimensions of the well are difficult to control. Because of the variations in the processes of manufacturing a BioFET, the sensing surface is non-uniform and the sensing signals are unstable.

A method 100 of fabricating a BioFET is illustrated in FIG. 1. The method 100 may include forming a BioFET using one or more process steps compatible with or typical to a complementary metal-oxide-semiconductor (CMOS) process. It is understood that additional steps can be provided before, during, and after the method 100, and some of the steps described below can be replaced or eliminated, for additional embodiments of the method. Further, it is understood that the method 100 includes steps having features of a typical CMOS technology process flow and thus, are only described briefly herein.

FIG. 1 is a flowchart of a method of manufacturing a BioFET as shown in FIGS. 2A-2K. In operation 101, a substrate is provided. In operation 102, a gate structure is formed over a first surface of the substrate. In operation 103, a source region and a drain region are formed in the substrate and adjacent to the gate structure. In operation 104, a channel region is formed to interpose the source and drain regions and underlying the gate structure. In operation 105, a first layer is formed over a second surface of the substrate opposite to the first surface. In operation 106, a second layer is formed over the first layer. In operation 107, a sensing film is formed over the channel region and over at least a portion of the first and second layers. In operation 108, a well is formed over the sensing film and cuts off the first layer and the second layer.

Figure 2A:
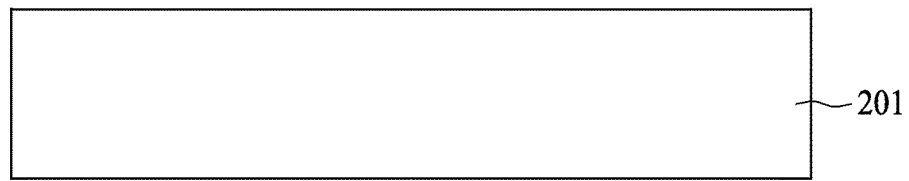
FIGS. 2A-2K are schematic diagrams illustrating a semiconductor structure of a BioFET in accordance with some embodiments.
Figure 2B:
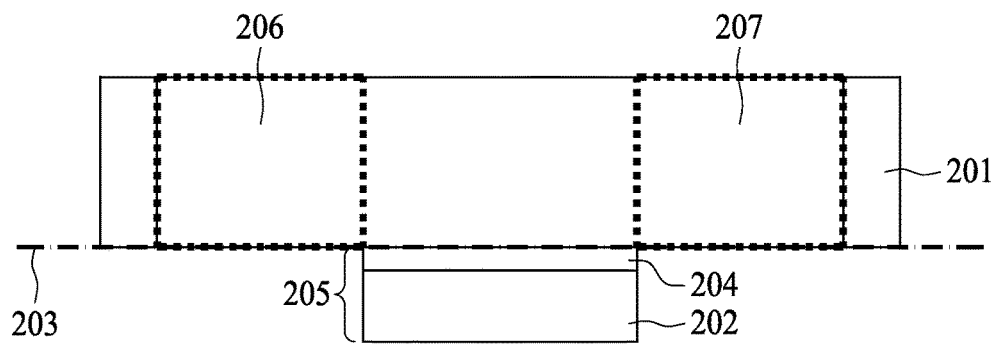
Figure 2C:
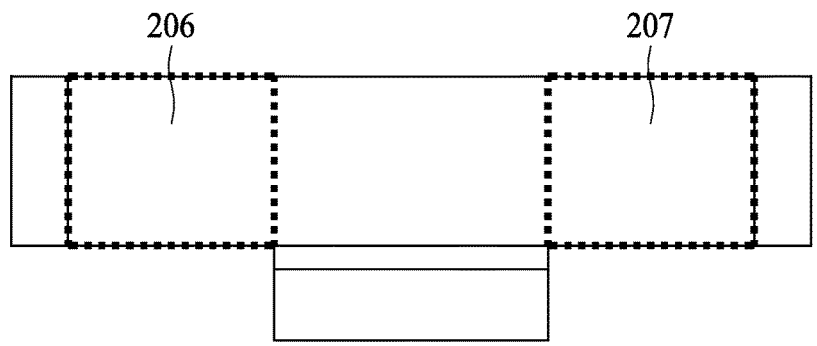
Figure 2D:
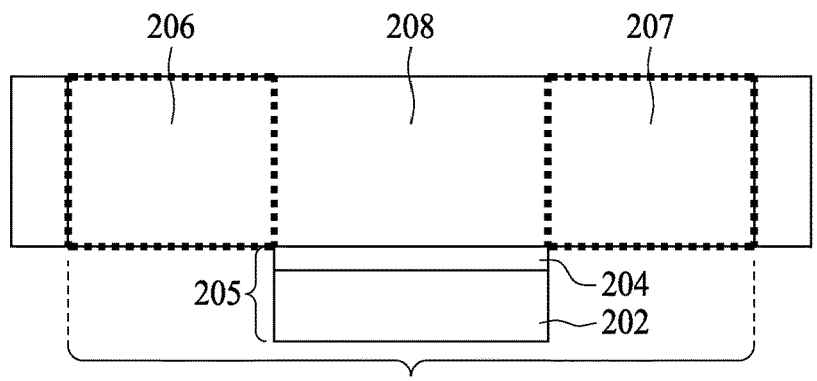
Figure 2E:
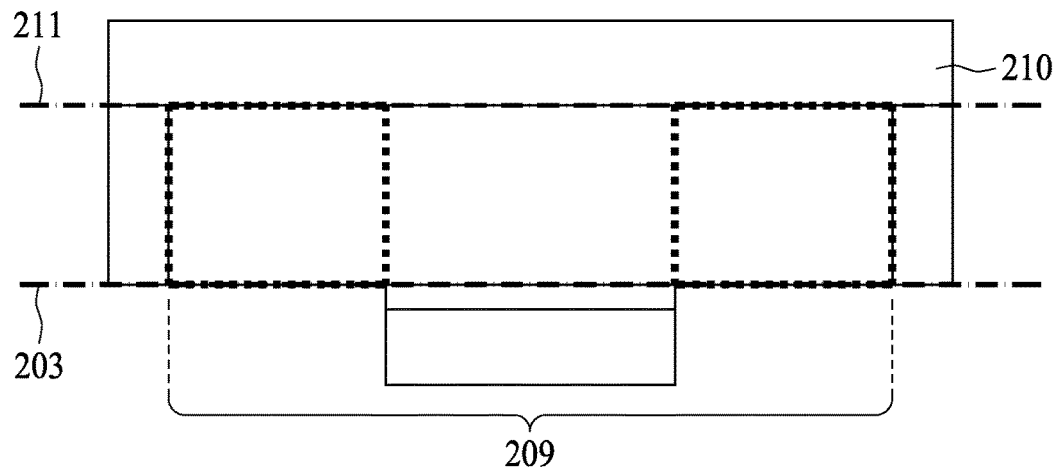
Figure 2F:
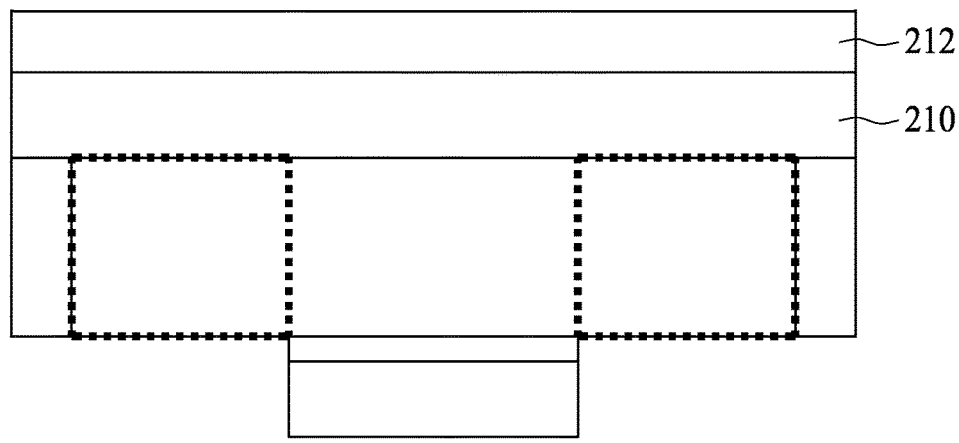
Figure 2G:
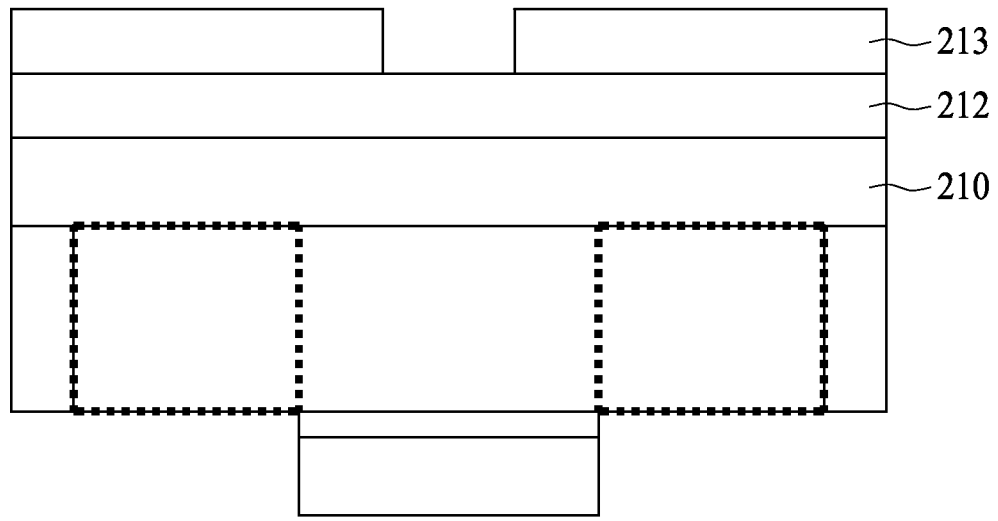
Figure 2H:
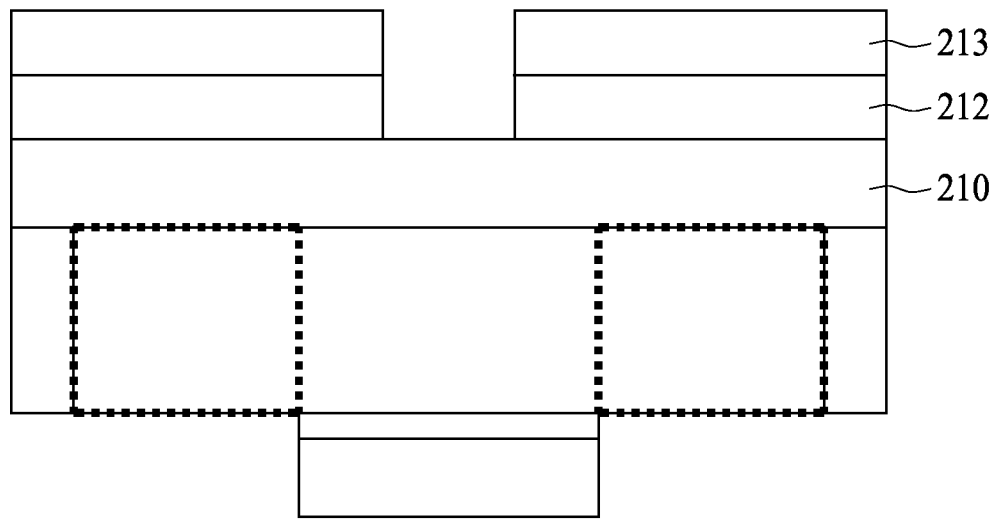
Figure 2I:
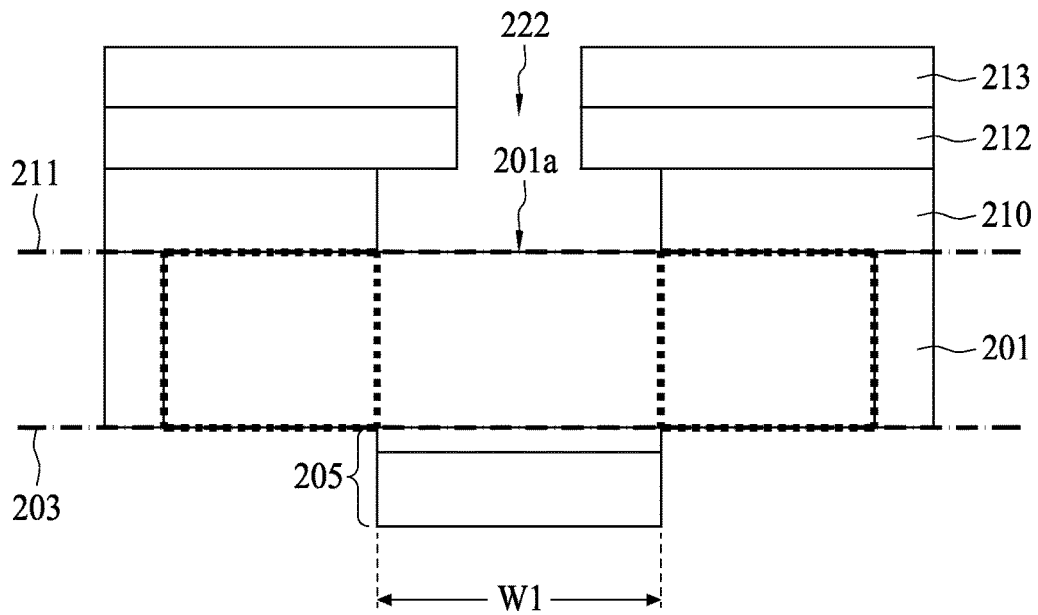
Figure 2J:
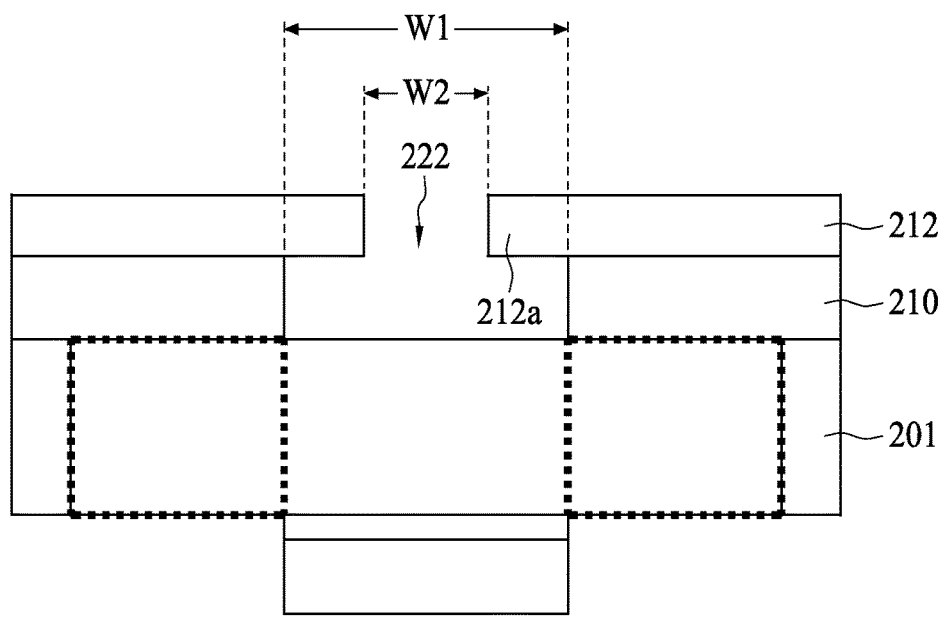
Figure 2K:
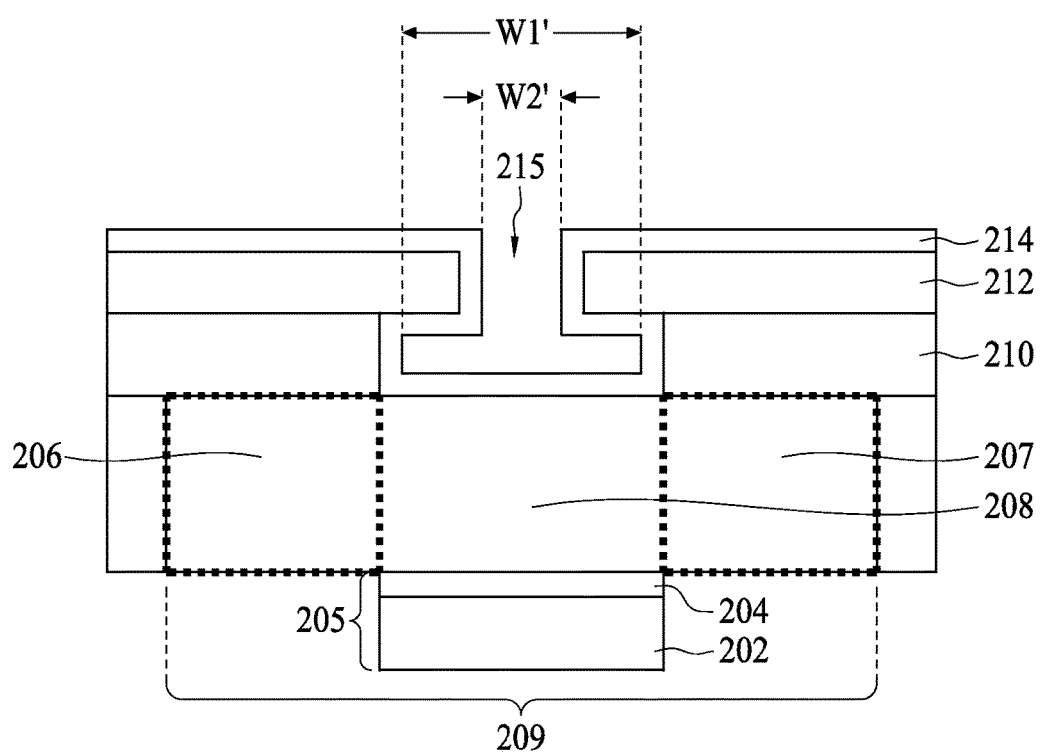

FIGS. 2A-2K schematically illustrate operations of the method of FIG. 1. In FIG. 2A, a substrate 201 is provided. FIG. 2A schematically illustrates the operation 101. In FIG. 2B, a gate structure 205 is formed over a first surface 203 of the substrate 201. The gate structure 205 comprises a gate electrode 202 and a gate dielectric layer 204 and/or other suitable layers. FIG. 2B schematically illustrates the operation 102. In FIG. 2C, a source region (206 or 207) and a drain region (206 or 207) in the substrate 201 adjacent to the gate structure 205 are formed. In some embodiments, the thicknesses of the source region and the drain region (206 and 207) are equal to or less than the thickness of the substrate 201. FIG. 2C schematically illustrates the operation 103. In FIG. 2D, a channel region 208 is formed to interpose the source region (206 or 207) and the drain region (206 or 207) and underlying the gate structure 205. FIG. 2D schematically illustrates the operation 104. The source and drain regions (206 and 207), the channel region 208 and the gate structure 205 form a field effect transistor (FET) 209. The FET 209 may be an n-type FET or a p-type FET. The source/drain regions (206 and 207) may comprise n-type dopants or p-type dopants depending on the FET configuration. In FIG. 2E, a first layer 210 is formed over a second surface 211 of the substrate 201 opposite to the first surface 203. FIG. 2E schematically illustrates the operation 105. In FIG. 2F, a second layer 212 is formed over the first layer 210. In some embodiments, the first layer 210 may be one of a nitride layer and an oxide layer, and the second layer 212 may be another one of a nitride layer and an oxide layer different from the first layer 210. FIG. 2F schematically illustrate the operation 106. In FIG. 2G, a photoresist 213 is formed and patterned over the second layer 212. In FIG. 2H, a portion of the second layer 212 not protected by the photoresist 213 is removed. In FIG. 2I, a portion of the first layer 210 is removed. In FIG. 2J, the photoresist 213 is removed. In FIG. 2K, a sensing film 214 is formed over the channel region 208 and over at least a portion of the first layer 210 and the second layer 212. A well 215 is formed over the sensing film 214 and cuts off the first layer 210 and the second layer 212. FIGS. 2G-2K schematically illustrate the operations 107 and 108. The semiconductor structure of FIG. 2K can be used to control dimensions of the well 215.

In some embodiments, the gate electrode 202 includes polysilicon. Other exemplary gate electrodes include metal gate electrodes including metal such as, Cu, W, Ti, Ta, Cr, Pt, Ag, Au; suitable metallic compounds like TiN, TaN, NiSi, CoSi; combinations thereof; and/or other suitable conductive materials. In some embodiments, the gate dielectric 204 is composed of silicon oxide. Other exemplary gate dielectrics include silicon nitride, silicon oxynitride, a dielectric with a high dielectric constant (high k) ranging from about 5 to about 100, and/or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The FET 209 may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), or spin on coating; etching including wet etching, dry etching, and plasma etching; and/or other suitable CMOS processes.

In some embodiments, the first layer 210 and the second layer 212 are adjacent and differ in etch rate to a predetermined etchant. As illustrated in FIG. 2I, the predetermined etchant can be the etchant used to remove the first layer 210 thereby exposing a surface 201a of the substrate 201. The exposed surface 201a of the substrate 201 is on an opposite side of the gate structure 205. In some embodiments, the exposed surface 201a is substantially located around the second surface 211 if the substrate 201 is highly resistant to the predetermined etchant. In some embodiments, the exposed surface 201a is proximal to the first surface 203 compared to the second surface 211. Therefore, a recessed portion of the second surface 211 might be observed wherein a lateral width $W_1$ of the recessed portion is defined by the removed portion of the first layer 210.

FIG. 2J illustrates the stacked structure including first layer 210 and second layer 212 over the second surface 211. In the stacked structure, a recess 222 is formed to expose a portion of the substrate 201. The sidewall of the recess 222 is in a stepped configuration. A portion of the sidewall is defined by the opening in the first layer 210. Another portion of the sidewall is defined by the opening in the second layer 212. The opening in the first layer 210 has a lateral width $W_1$, which is greater than the lateral width $W_2$ of the second layer. Relative to the first layer 210, the second layer 212 has a protrusion 212a extended inwardly toward the center of the recess 222, therefore making the opening of the recess 222 being smaller than its closed end.

In some embodiments, the first layer 210 and the second layer 212 may be one of a nitride layer and an oxide layer. In some embodiments, the first layer 210 and the second layer 212 are made of different materials. In some embodiments, the first layer 210 is a nitride layer. In some embodiments, the first layer 210 is a silicon nitride layer. In some embodiments, the second layer 212 is an oxide layer. In some embodiments, the second layer 212 is a silicon oxide layer. The oxide layer and nitride layer have high etching selectivities of oxide to nitride. The oxide layer and nitride layer can also be etch stop layers for each other. In some embodiments, the thickness of the second layer 212 is greater than that of the first layer 210. For example, the thickness of the first layer 210 is 1000 angstrom and that of the second layer 212 is 8000 angstrom. In some embodiments, a portion of the second layer 212 is removed by etching. An etchant for etching the second layer 212 stops etching on the first layer 210. The etchant may have a selectivity of oxide to nitride greater than 10. In some embodiments, a portion of the first layer 210 is removed by using materials such as $H_3PO_4$. The material removes a portion of the first layer 210 and stops on the second surface 211 of the substrate 201. In some embodiments, the removed portions of the first layer 210 and that of the second layer 212 may be different.

In some embodiments, the sensing film 214 is made of a high-k material. In some embodiments, the sensing film 214 is selected from the group comprising $Si_3N_4$, $Al_2O_3$, $TiO_2$, $HfO_2$, $Ta_2O_5$, $SnO_2$ and combinations thereof. In some embodiments, the thickness of the sensing film 214 is about 30 angstrom to about 100 angstrom. As a further example, exemplary sensing film 214 include $HfO_2$, $Ta_2O_5$, Pt, Au, W, Ti, Al, Cu, oxides of such metals, $SiO_2$, $Si_3N_4$, $Al_2O_3$, $TiO_2$, TiN, $ZrO_2$, SnO, $SnO_2$; and/or other suitable materials. The sensing film 214 may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). In some embodiments, the sensing film 214 may include a plurality of layers.

In some embodiments, the sensing film 214 is considered as a conformal layer capping on the stacked structure over the second surface 211. As in FIG. 2K, the sensing film 214 substantially follows the profile of the recess 222 in FIG. 2J so as to form a well 215 with similar feature of the stacked first layer 210 and the second layer 212. The sidewall of the well 215 is also in a stepped configuration. A portion of the well 215 is defined by the opening in the first layer 210 and the thickness of the sensing film 214. Another portion of the well 215 is defined by the opening in the second layer 212 and the thickness of the sensing film 214. The well 215 has at least two different lateral widths, wherein $W_2$ is the lateral width of the portion close to the opening of the well 215 and $W_1'$ is the lateral width of the portion close to the closed end of the well 215. The closed end of the well 215 is also configured as a surface for receiving the biomolecules.

Figure 2L:
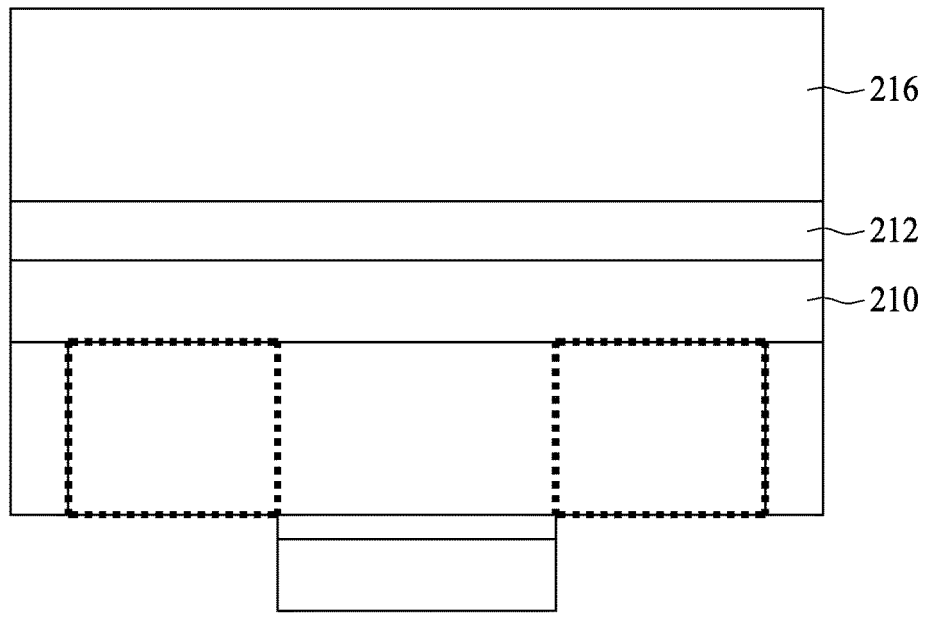
FIGS. 2L-2R are schematic diagrams illustrating a semiconductor structure of a BioFET in accordance with some embodiments.
Figure 2M:
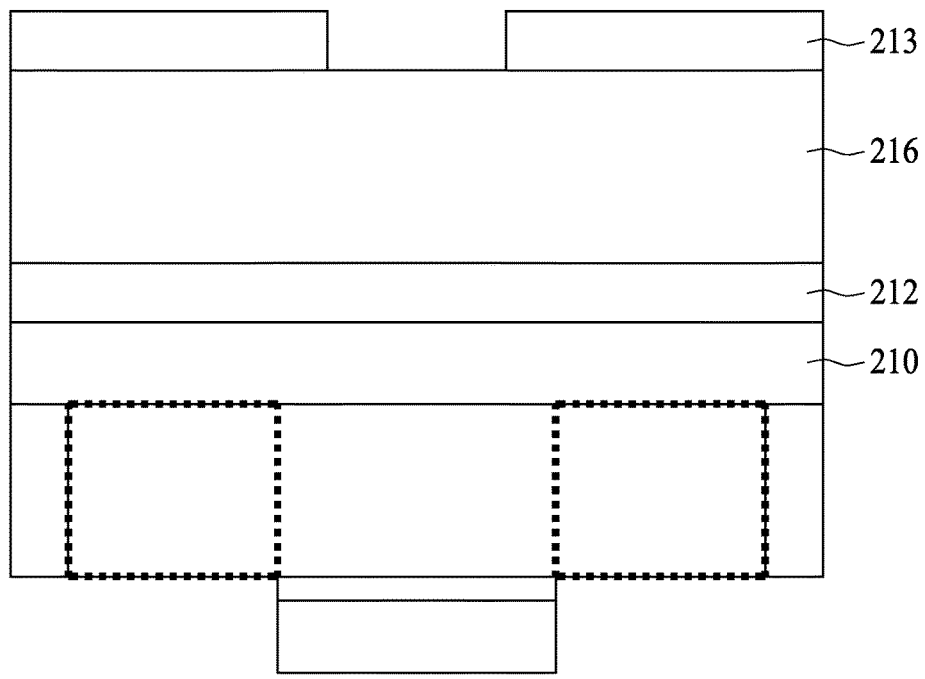
Figure 2N:
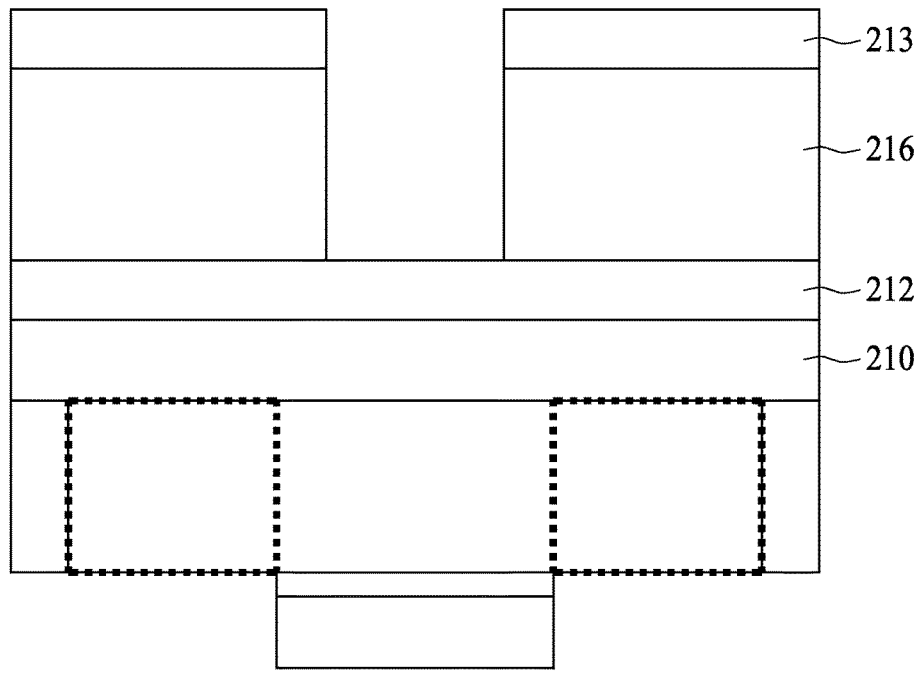
Figure 2O:
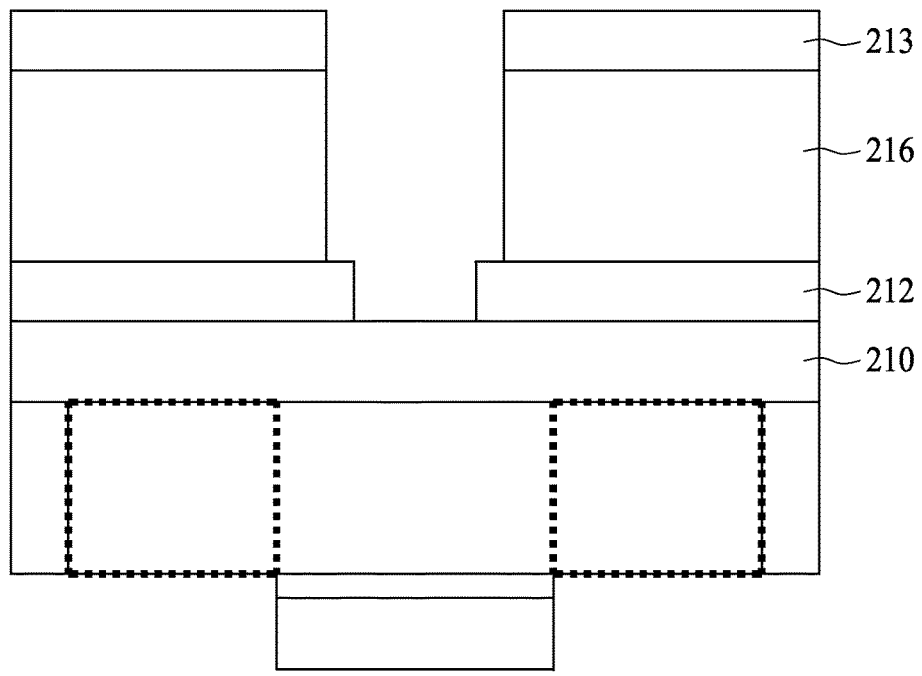
Figure 2P:
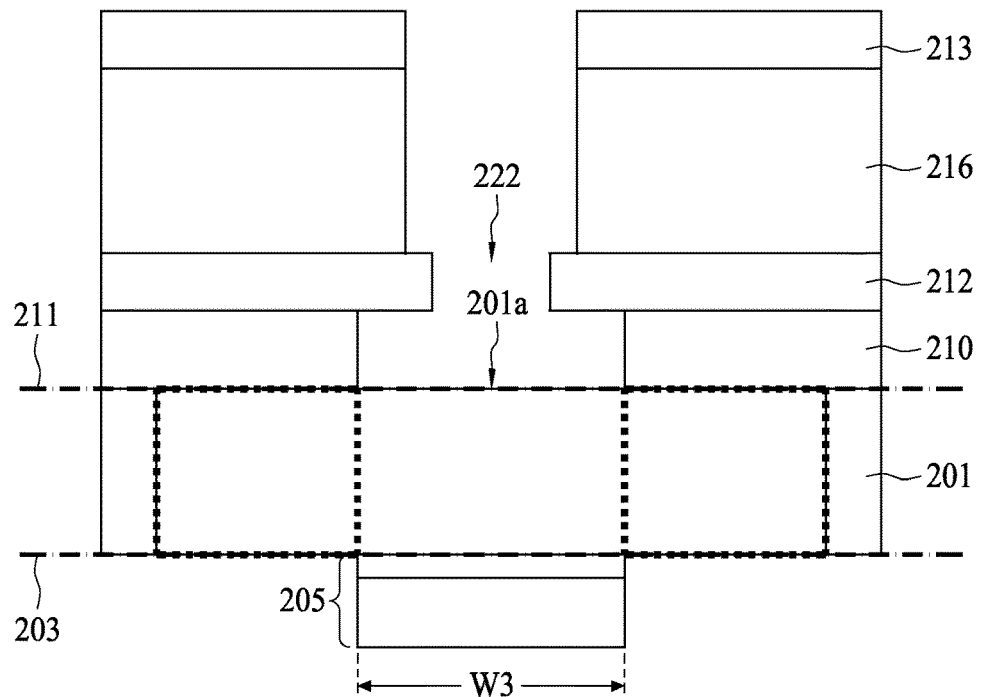
Figure 2Q:
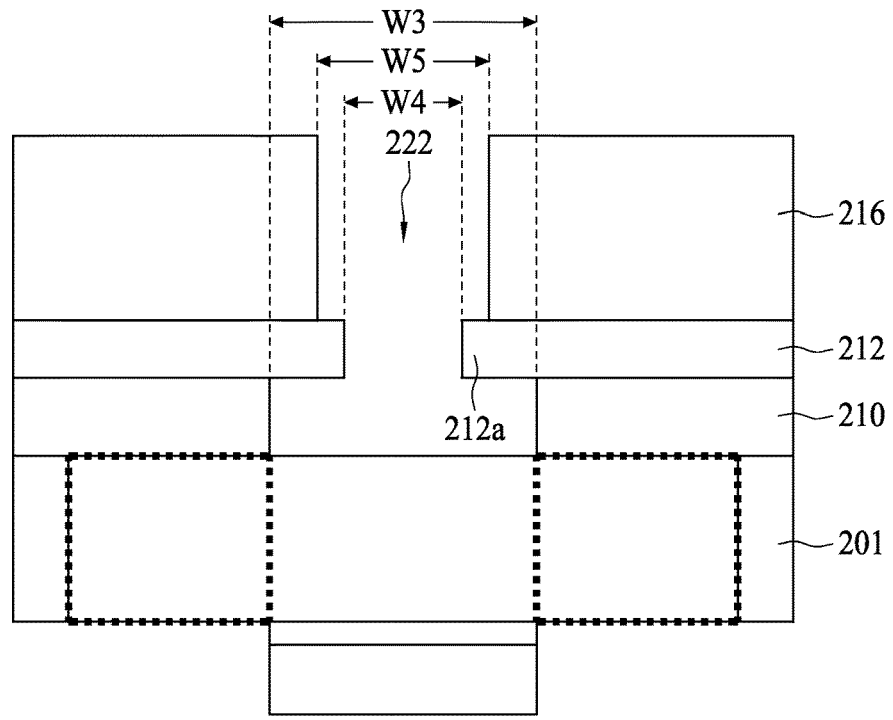
Figure 2R:
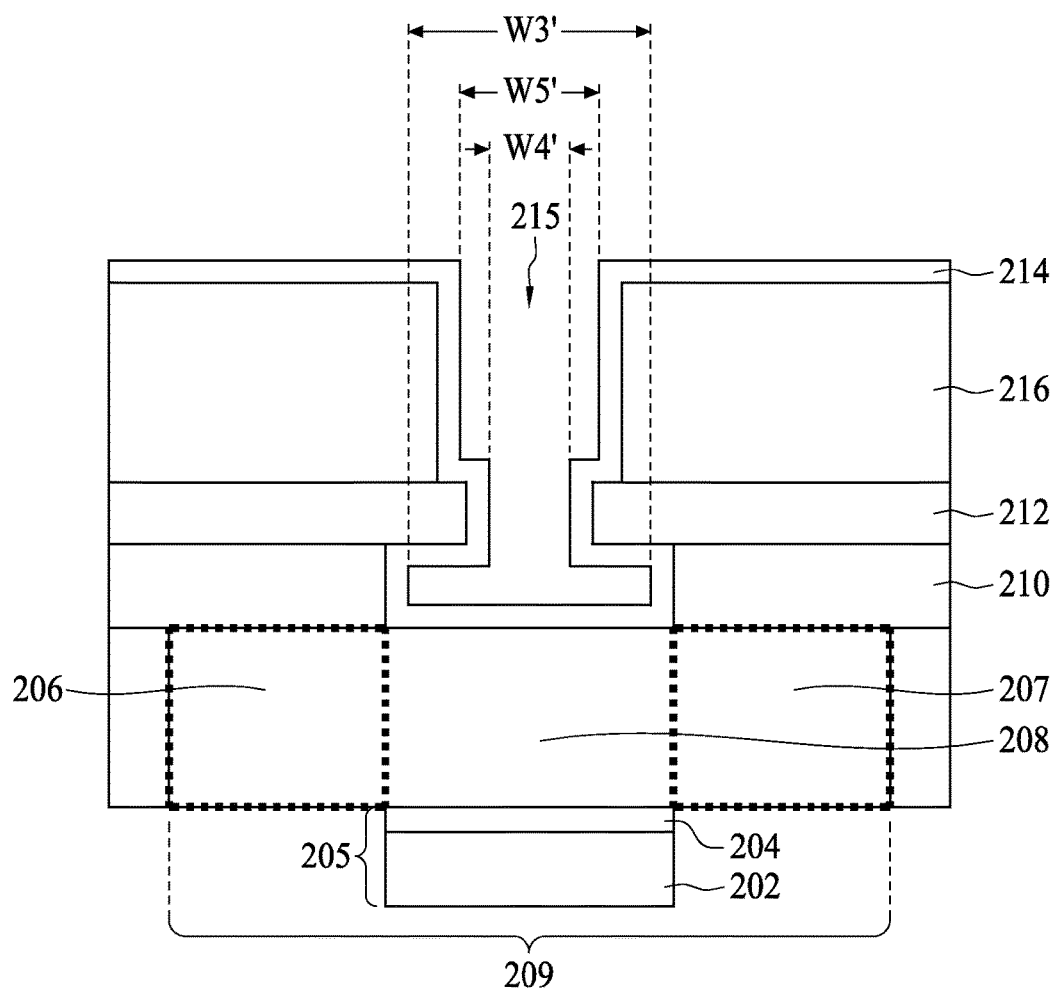

Referring back to FIG. 2F, the second layer 212 is formed over the first layer 210. In some embodiments, a third layer 216 can be formed over the second layer 212. Referring to FIG. 2L, a third layer 216 is formed over the second layer 212. In some embodiments, the third layer 216 is deposited over the second layer 212. In FIG. 2M, a photoresist 213 is formed and patterned over the third layer 216. In FIG. 2N, a portion of the third layer 216 not protected by the photoresist 213 is removed. In FIG. 2O, a portion of the second layer 212 is removed. In FIG. 2P, a portion of the first layer 210 is removed. In FIG. 2Q, the photoresist 213 is removed. In FIG. 2R, a sensing film 214 is formed over the channel region 208 and over at least a portion of the first layer 210, the second layer 212 and the third layer 216. A well 215 is formed over the sensing film 214 and cuts off the first layer 210, the second layer 212 and the third layer 216.

In some embodiments, the third layer 216 is one of a nitride layer and an oxide layer. In some embodiments, the material of the third layer 216 is the same as that of the first layer 210. In some embodiments, the thickness of the third layer 216 is greater than that of the first layer 210 and the second layer 212. For example, the thickness of the third layer 216 is 8000 angstrom, the thickness of the first layer 210 is 1000 angstrom and the thickness of the second layer 212 is also 1000 angstrom. The first, second, and third layers can each be an etch stop layer for one another. In some embodiments, a portion of the third layer 216 is removed by etching. A first etchant for etching the third layer 216 stops etching on the second layer 212. The first etchant may have a selectivity of oxide to nitride greater than 10. In some embodiments, a portion of the second layer 21 is removed by etching. A second etchant for etching the second layer 212 stops etching on the first layer 210. The second etchant may have a selectivity of oxide to nitride different from the first etchant. In some embodiments, the second etchant may have a lesser selectivity of oxide to nitride than the first etchant. For example, the second etchant may have a selectivity of oxide to nitride greater than 5. In some embodiments, a portion of the first layer 210 is removed using a material such as a buffer oxide etch (BOE). The material removes the portion of the first layer 210 and stops on the second surface 211 of the substrate 201. In some embodiments, the removed portions of the first layer 210, the second layer 212 and the third layer 216 may be different. In some embodiments, the width of the removed portion of the third layer 216 and that of the first layer 210 are greater than that of the second layer 212. The semiconductor structure of FIG. 2R can be used to control dimensions of the well 215.

In some embodiments, the first layer 210, the second layer 212 and the third layer 216 are adjacent and differ in etch rate to a predetermined etchant. As illustrated in FIG. 2P, the predetermined etchant can be the etchant used to remove the first layer 210 thereby exposing a surface 201a of the substrate 201. The exposed surface 201a of the substrate is on an opposite side of the gate structure 205. In some embodiments, the exposed surface 201a is substantially located around the second surface 211 if the substrate 201 is highly resistant to the predetermined etchant. In some embodiments, the exposed surface 201a is proximal to the first surface 203 compared to the second surface 211. Therefore, a recessed portion of the second surface 211 might be observed. The recessed portion of the second surface 211 has a lateral width $W_3$ which is defined by the removed portion of the first layer 210.

FIG. 2Q illustrates the stacked structure including first layer 210, the second layer 212 and the third layer 216 over the second surface 211. In the stacked structure, a recess 222 is formed to expose a portion of the substrate 201. The sidewall of the recess 222 is in a stepped configuration. One portion of the sidewall is defined by the opening in the first layer 210. Another portion of the sidewall is defined by the opening in the second layer 212. The other portion of the sidewall is defined by the opening in the third layer 216. The opening in the first layer 210 has a lateral width $W_3$, which is greater than the lateral width $W_4$ of the second layer. The opening in the third layer 216 has a lateral width $W_5$, which is greater than the lateral width $W_4$ of the second layer. The lateral width $W_5$ of the opening in the third layer 216 may be greater than, equal to or less than the lateral width $W_3$ of the first layer 210. Relative to the first layer 210, the second layer 212 has a protrusion 212a extended inwardly toward the center of the recess 222.

In some embodiments, the sensing film 214 is considered as a conformal layer capping on the stacked structure and over the second surface 211. As in FIG. 2R, the sensing film 214 substantially follows the profile of the recess 222 in FIG. 2Q so as to form a well 215 with similar feature of the stacked first layer 210, second layer 212 and third layer 216. The sidewall of the well 215 is also in a stepped configuration. One portion of the well 215 is defined by the opening in the first layer 210 and the thickness of the sensing film 214. Another portion of the well 215 is defined by the opening in the second layer 212 and the thickness of the sensing film 214. The other portion of the well 215 is defined by the opening in the third layer 216 and the thickness of the sensing film 214. The well 215 has three different lateral widths, wherein $W_4'$ is the lateral width of the portion of the middle of the opening of the well 215, $W_3'$ is the lateral width of the portion close to the closed end of the well 215, and $W_5'$ is the lateral width of the portion close to the opening of the well 215. The closed end of the well 215 is also configured as a surface for receiving the biomolecules.

Figure 3A:
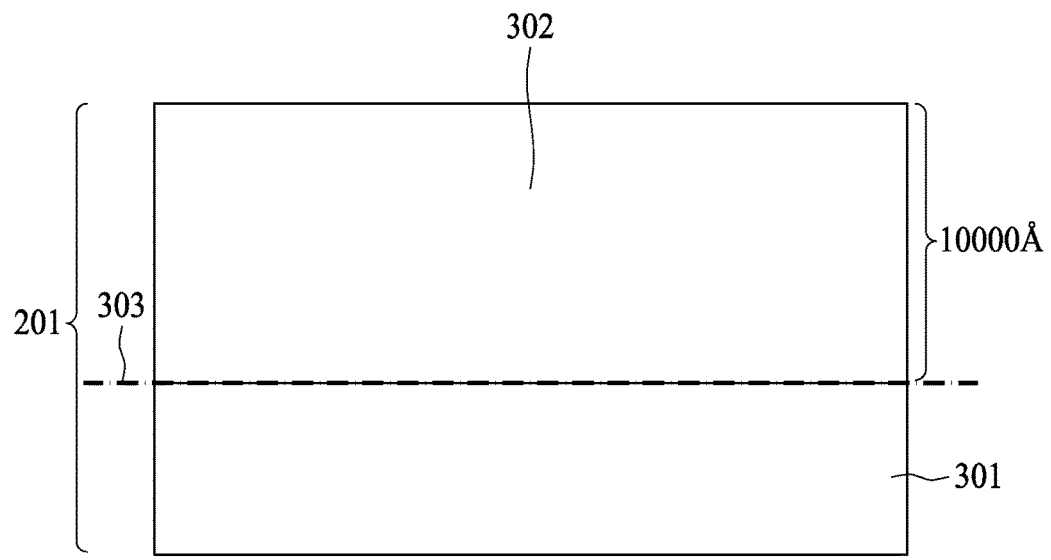
FIGS. 3A-3C are schematic diagrams illustrating a substrate of a BioFET in accordance with some embodiments.
Figure 3B:
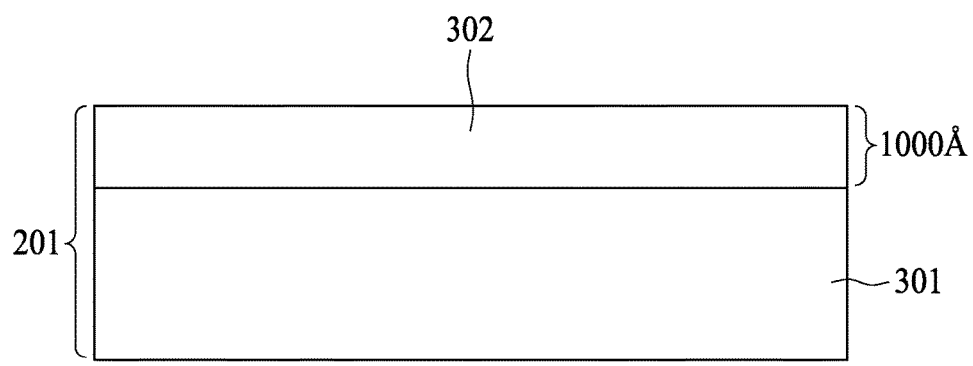
Figure 3C:
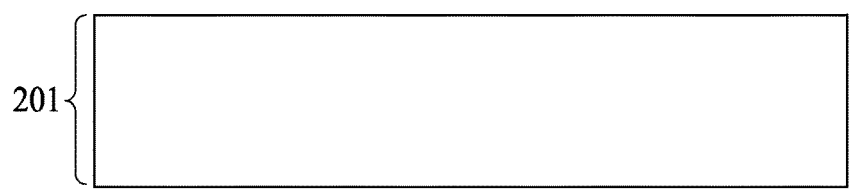

In some embodiments, the substrate 201 in FIG. 2A is a semiconductor on insulator (SOI) substrate. As shown in FIG. 3A, a SOI substrate 201 may include a buried oxide (BOX) layer 302 formed over a semiconductor layer 301. The BOX layer 302 may be formed by a process such as separation by implanted oxygen (SIMOX), and/or other suitable processes. A first surface of the SOI substrate 201 is the device side where the gate structure 209 is formed. In some embodiments, the thickness of the BOX layer 302 is initially 10,000 angstrom, as shown in FIG. 3A. In some embodiments, the BOX layer 302 is thinned down to 1000 angstrom by BOE, as shown in FIG. 3B. In some embodiments, the removal of the BOX layer 302 may be accomplished by mechanical or chemical means. For example, mechanical means includes polishing or grinding, such as chemical mechanical polishing (CMP). A chemical means includes wet etch, such as HNA or TMAH, or dry etch including plasma and non-plasma etch. In some embodiments, a portion of the BOX layer 302 may be remained and configured as the first layer 210, as shown in FIG. 3B. In some embodiments, the BOX layer 302 of the SOI substrate 201 is completely removed. Under such condition, the substrate 201 is a semiconductor substrate, as shown in FIG. 3C. In some embodiments, the BOX layer 302 is removed to expose a second surface 303 of the SOI substrate 201. The substrate 201 in FIG. 3C may be a silicon substrate. Alternatively, the substrate 201 may comprise another elementary semiconductor, such as germanium; a compound semiconductor including silicon carbide; an alloy semiconductor including silicon germanium; or combinations thereof.

Figure 4:
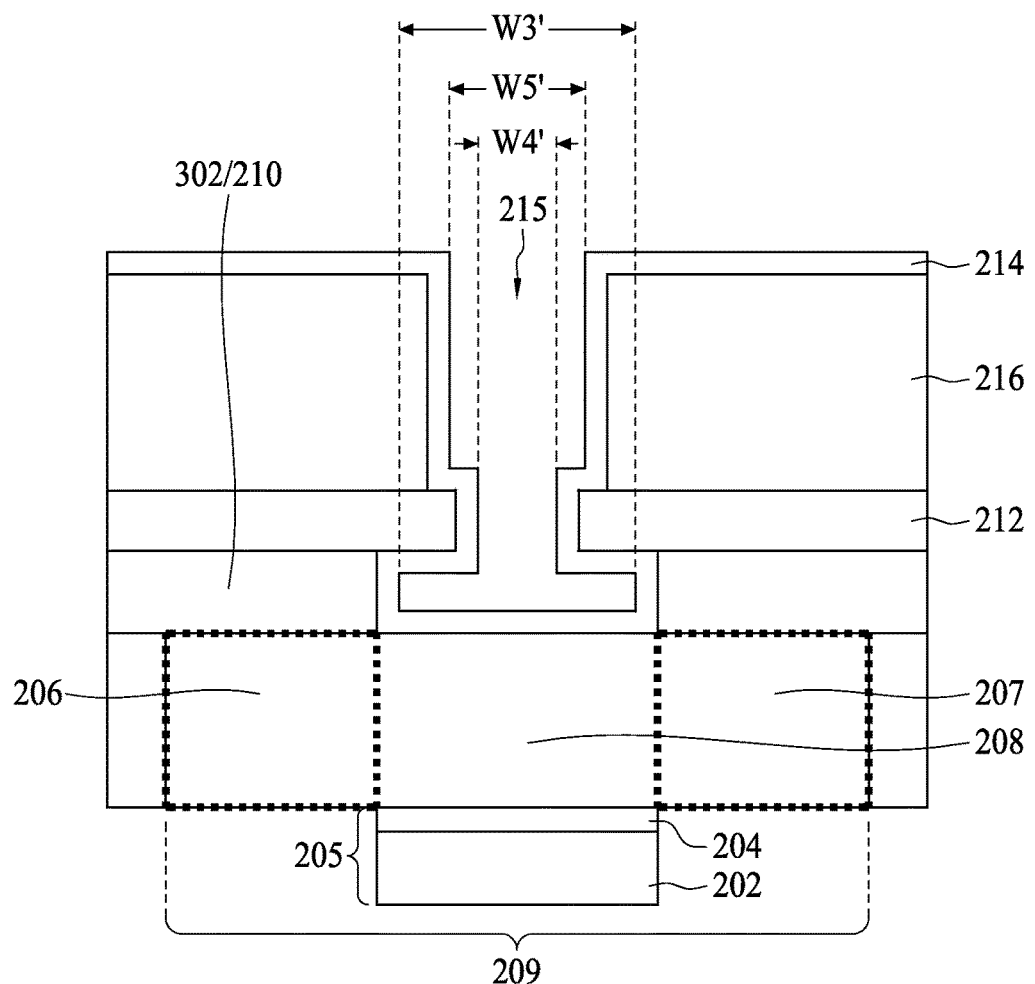
FIG. 4 is a schematic diagram illustrating a semiconductor structure of a BioFET in accordance with some embodiments.

The same reference numerals in different drawings refer to the same element. FIG. 4 illustrates a semiconductor structure formed with the substrate 201 in FIG. 3B. The difference between the structure in FIGS. 4 and 2R is that the first layer 210 in FIG. 4 is formed from a portion of the BOX layer 302 in FIG. 3B while the first layer 210 in FIG. 2R is formed with the substrate 201 in FIG. 3C. The other operations for manufacturing the semiconductor structure shown in FIGS. 2R and 4 are substantially the same. Relative to the first layer 210, the second layer 212 has a protrusion 212a extended inwardly toward the center of the well 215, therefore forming a necking portion in the well 215.

Figure 5A:
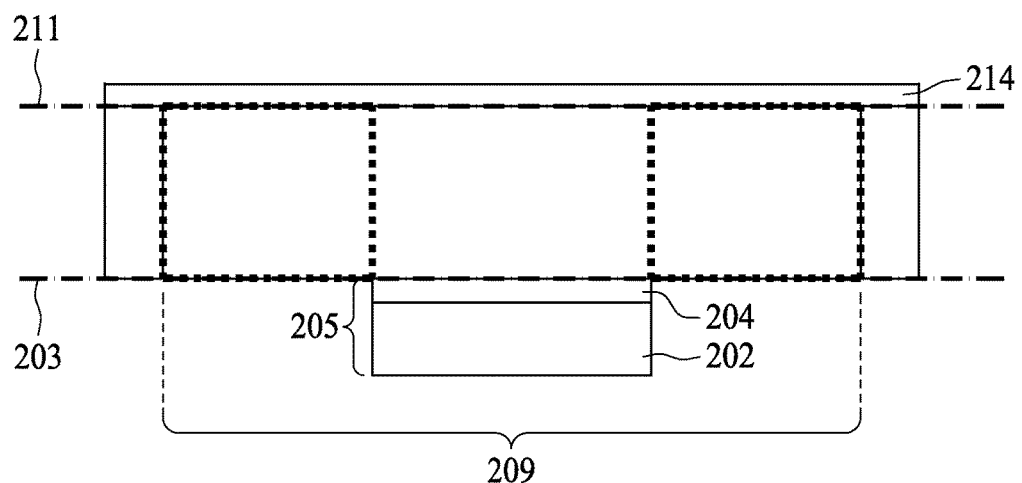
FIGS. 5A-5I are schematic diagrams illustrating a semiconductor structure of a BioFET in accordance with some embodiments.
Figure 5B:
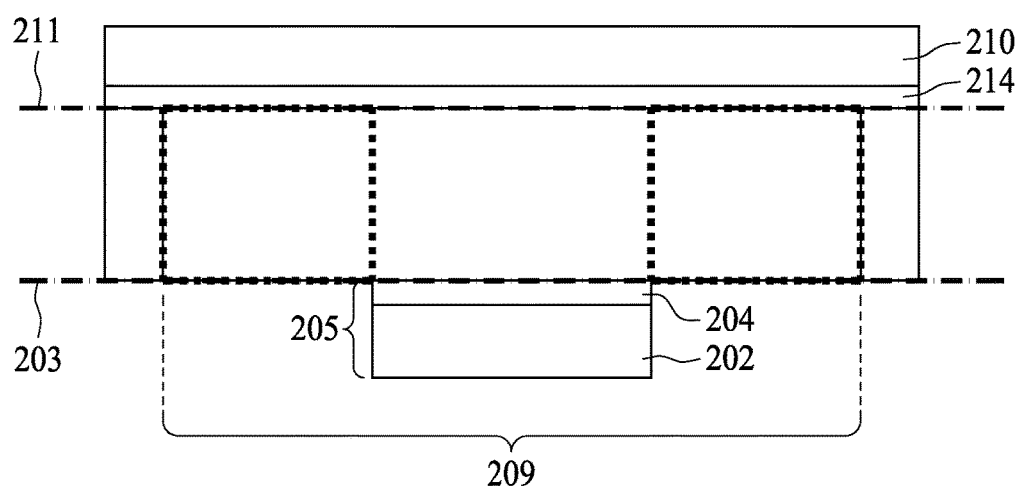
Figure 5C:
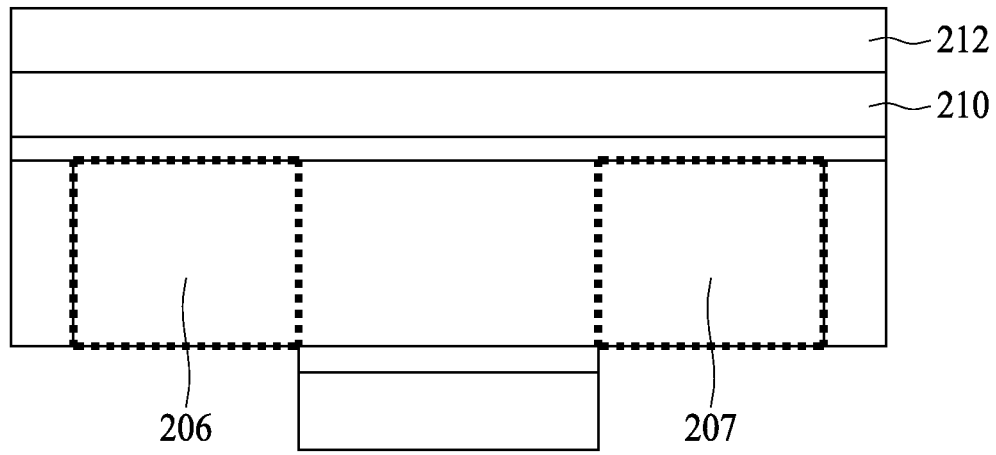
Figure 5D:
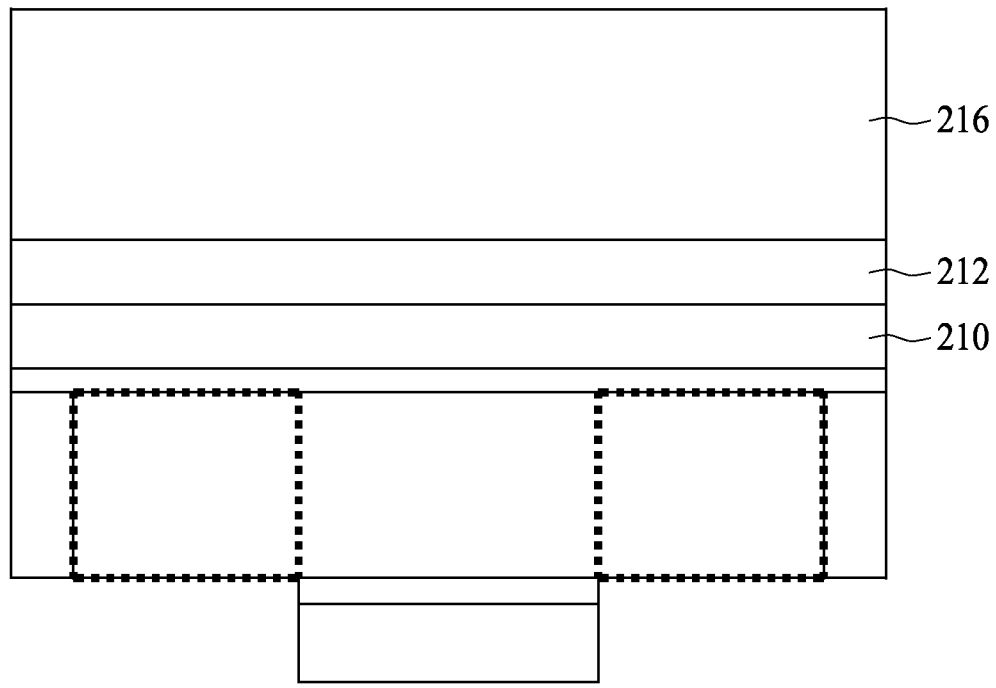
Figure 5E:
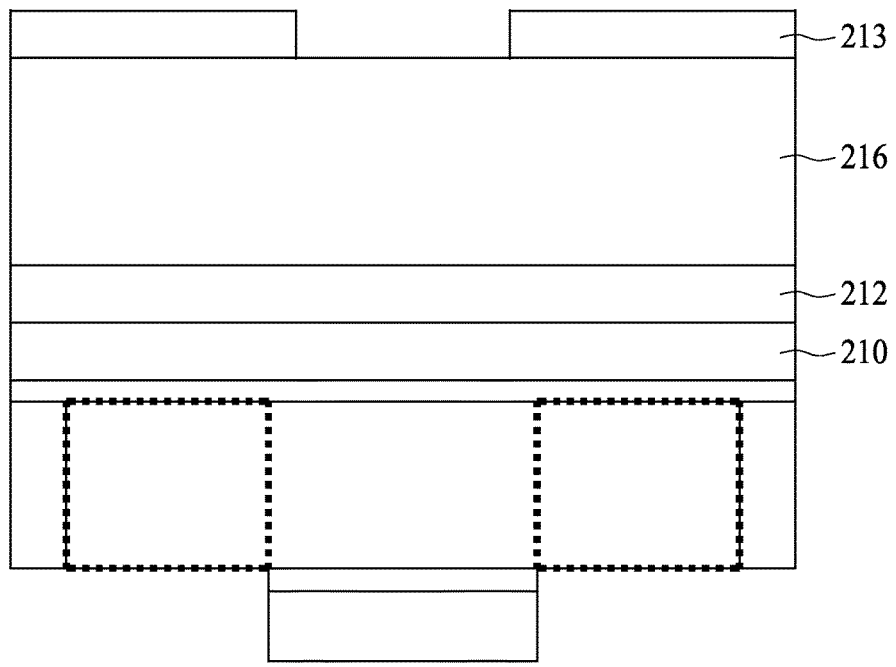
Figure 5F:
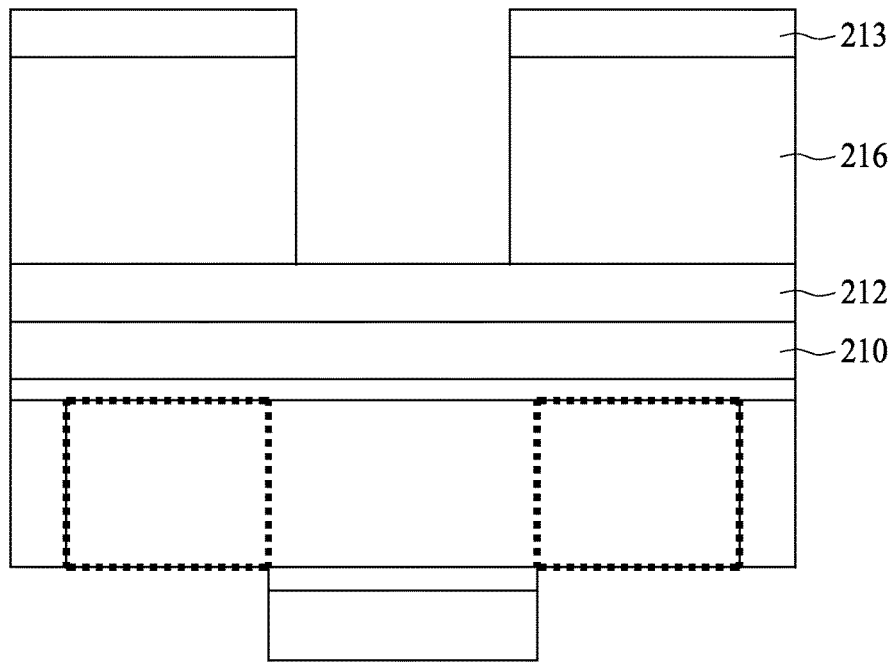
Figure 5G:
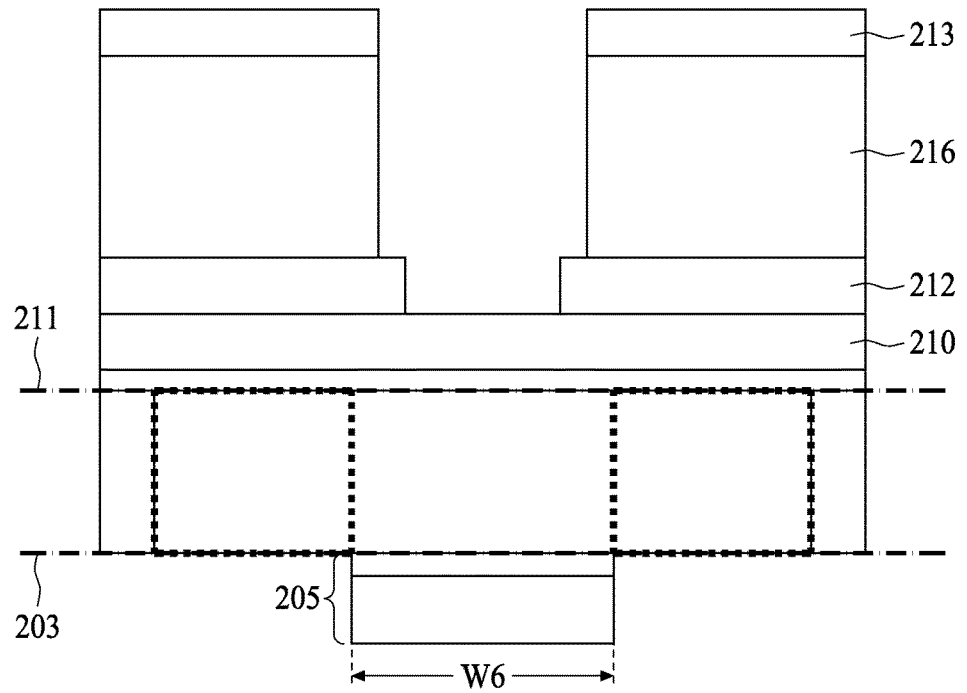
Figure 5H:
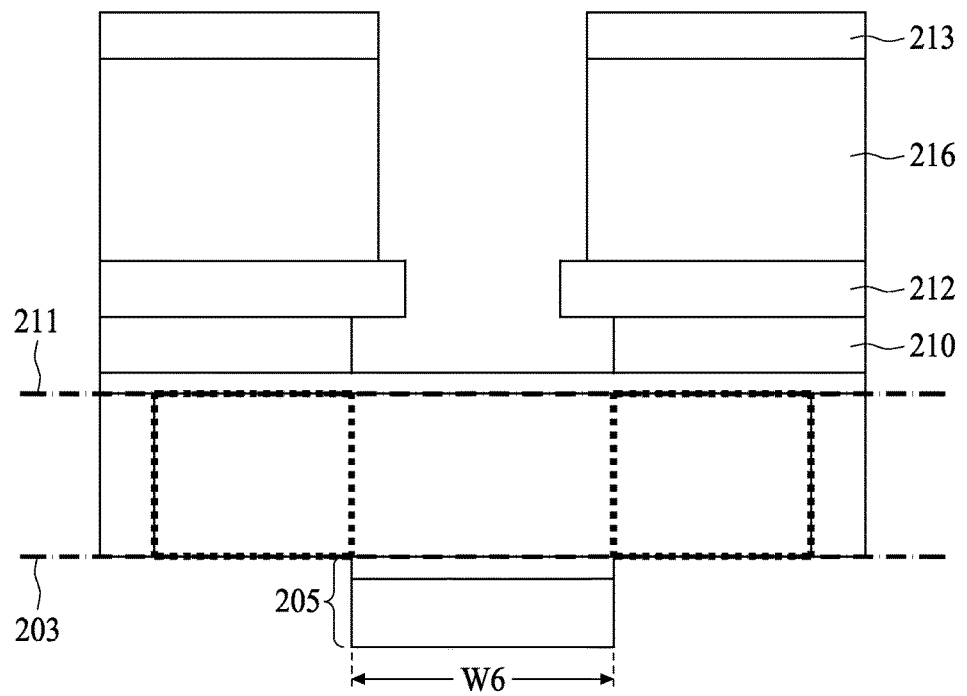
Figure 5I:
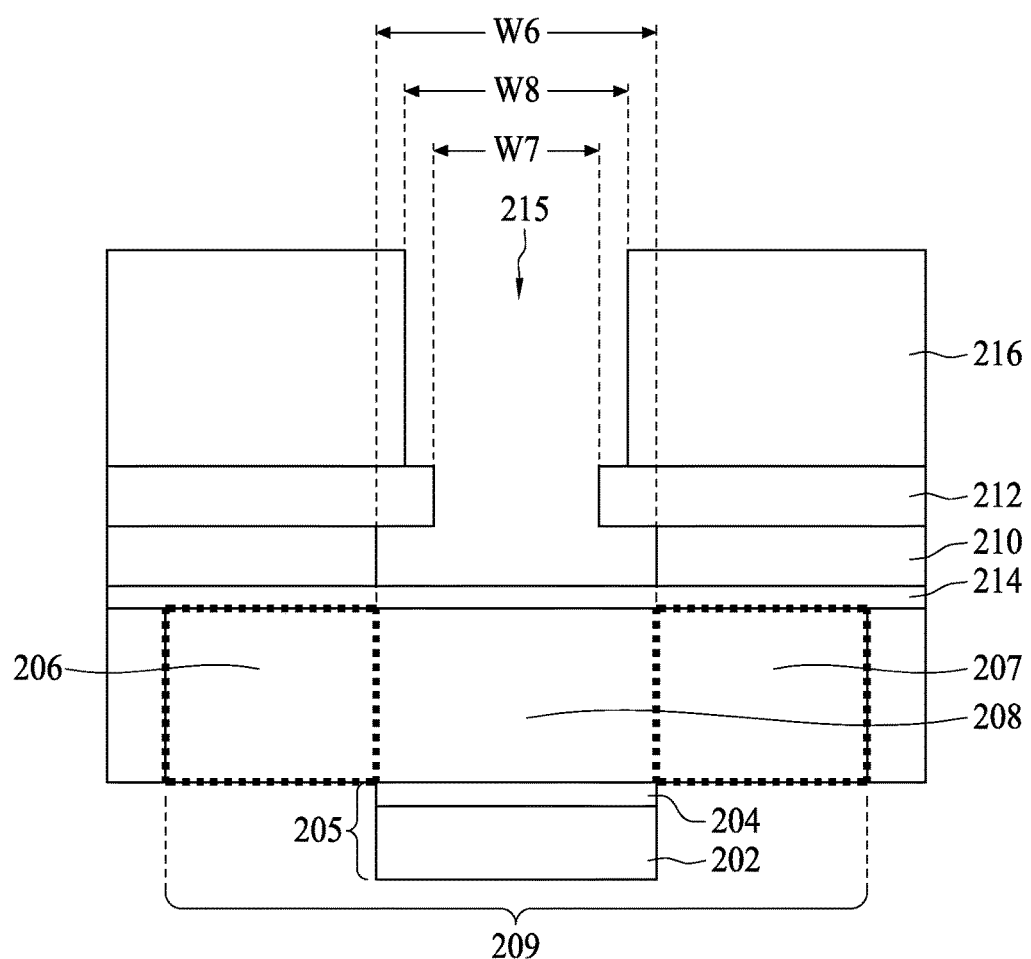

In some embodiments, the sensing film 214 may be formed prior to forming the first layer 210. In FIG. 5A, a field effect transistor (FET) 209 is provided. A sensing film 214 is formed over the second surface 211 of the substrate 201 opposite to the first surface 203. In FIG. 5B, a first layer 210 is formed over the sensing film 214. In FIG. 5C, a second layer 212 is formed over the first layer 210. In some embodiments, the first layer 210 may be one of a nitride layer and an oxide layer, and the second layer 212 may be another one of a nitride layer and an oxide layer different from the first layer 210. In FIG. 5D, a third layer 216 is formed over the second layer 212. In FIG. 5E, a photoresist 213 is formed and patterned over the third layer 216. In FIG. 5F, a portion of the third layer 216 not protected by the photoresist 213 is removed. In FIG. 5G, a portion of the second layer 212 is removed. In FIG. 5H, a portion of the first layer 210 is removed. In FIG. 5I, the photoresist 213 is removed. A well 215 is formed over the sensing film 214 and cuts off the first layer 210, the second layer 212 and the third layer 216. The semiconductor structure of FIG. 5I can be used to control dimensions of the well 215.

FIG. 5I illustrates the stacked structure including first layer 210, the second layer 212 and the third layer 216 over the second surface 211. In some embodiments, the opening in the first layer 210 has a lateral width $W_6$, which is greater than the lateral width $W_7$ of the second layer 212. The opening in the third layer 216 has a lateral width $W_8$, which is also greater than the lateral width $W_7$ of the second layer 212. In some embodiments, the lateral width $W_8$ of the opening in the third layer 216 may be greater than, equal to or less than the lateral width $W_6$ of the first layer 210. In some embodiments, the lateral lengths $W_6$, $W_7$ and $W_8$ may be the same. In some embodiments, relative to the first layer 210, the second layer 212 has a protrusion 212a extended inwardly toward the center of the well 215.

As in FIG. 5I, the sensing film 214 substantially overlies on the second surface 211 of the substrate. The sidewall of the well 215 is in a stepped configuration. One portion of the well 215 is defined by the opening in the first layer 210. Another portion of the well 215 is defined by the opening in the second layer 212. The other portion of the well 215 is defined by the opening in the third layer 216. The well 215 has three lateral widths, wherein $W_7$ is the lateral width of the portion of a necking portion of the opening of the well 215, $W_6$ is the lateral width of the portion close to the closed end of the well 215 and $W_8$ is the lateral width of the portion close to the opening of the well 215. The closed end of the well 215 is also configured as a surface for receiving the biomolecules.

Figure 6A:
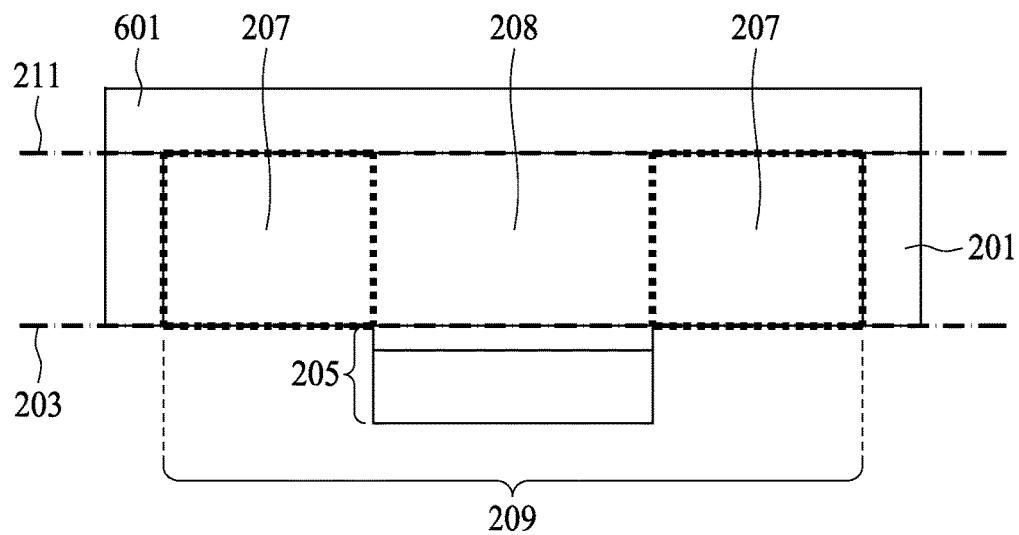
FIGS. 6A-6J are schematic diagrams illustrating a semiconductor structure of a BioFET in accordance with some embodiments.
Figure 6B:
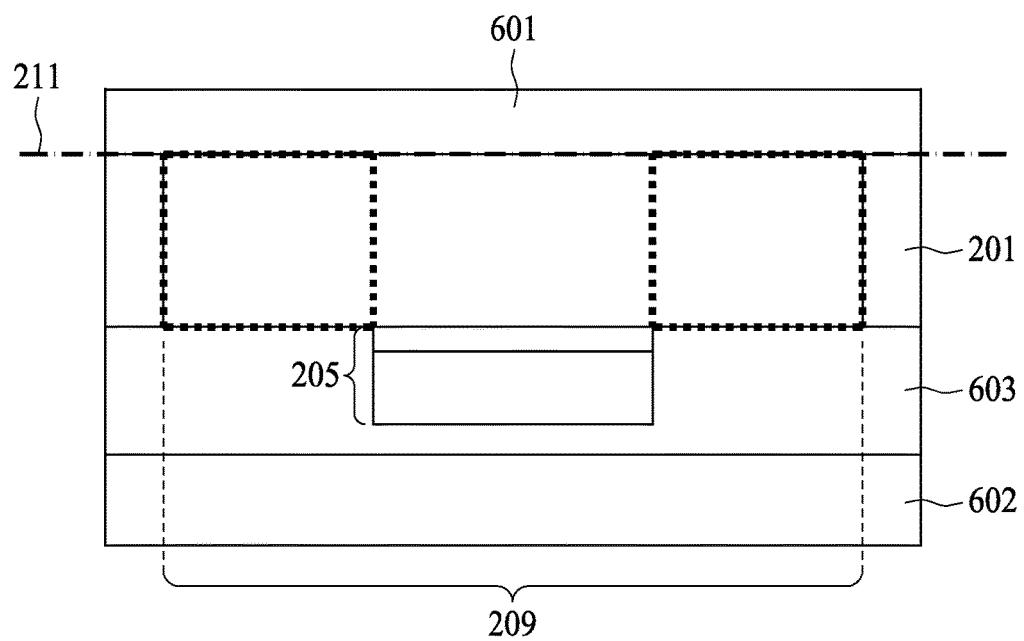

Referring to FIG. 6A, the FET device 209 includes a gate structure 205 formed over a first surface 203 of the substrate 201 and a channel region 208 in the substrate 201 below the gate structure 205. A BOX layer 601 is formed over a second surface 211 of the substrate 201. Referring to FIG. 6B, the first surface 203 of the substrate 201 is attached to a carrier substrate 602. In some embodiments, additional layer(s) 603 is formed over the FET 209, including metal interconnect layers, dielectric layers, passivation layers, bonding metal layers, and any other material layers typically formed to complete a semiconductor device. In FIG. 6B, a layer 603 is disposed over the FET 209 between the FET 209 and a carrier substrate 602. The layer 603 may include a multi-layer interconnect (MLI) structure. The MLI structure may include conductive lines, conductive vias, and/or interposing dielectric layers (e.g., interlayer dielectric (ILD)). The MLI structure may provide physical and electrical connections to the FET 209 at the source and drain regions (206 and 207) and at the gate electrode layer 202. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FGS), SILK (a product of Dow Chemical of Michigan), BLACK DIAMOND (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

The carrier substrate 602 is attached to the substrate by bonding. In some embodiments, the carrier substrate 602 is bonded to the last MLI layer. In an embodiment, the carrier substrate is bonded to a passivation layer formed on the MLI and/or ILD layers of the substrate. The carrier substrate 602 may be attached to the substrate 201 using fusion, diffusion, eutectic bonding, and/or other suitable bonding methods. Exemplary compositions for the carrier substrate 602 include silicon, glass, and quartz. In some embodiments, the carrier substrate 602 may include other functionalities such as; interconnect features, bonding sites, defined cavities, and/or other suitable features.

Figure 6C:
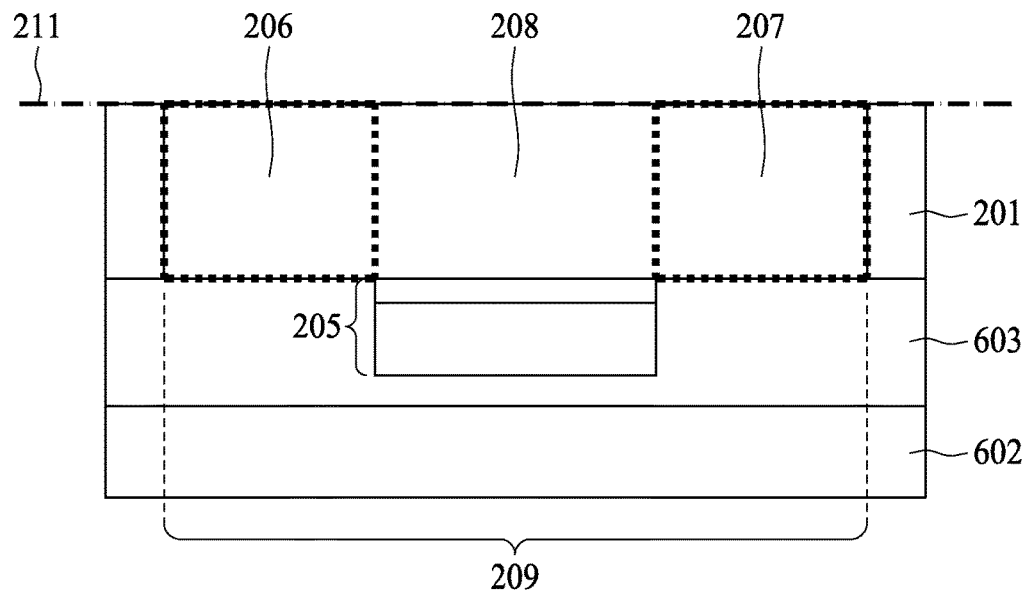

Referring to FIG. 6C, the channel region 208 of the FET 209 is exposed away from the second surface 211 of the substrate 201. Depending on the type of substrate 201, a number of methods may be used to expose the channel region 208. In some embodiments, the substrate 201 is formed with an SOI substrate. The BOX layer of the SOI substrate is first thinned until the second surface 211 of the substrate 201. A first thinning may be accomplished by grinding, wet etch, dry etch, plasma etch and/or other suitable processes. In order to avoid plasma induced damage (PID) with residual charge at the channel region 208 of the FET 209, a non-plasma etch is used in this operation or at least as the last thinning step. In some embodiments, a wet etch or a non-plasma dry etch is used to thin the entire substrate 201 from the second surface 211 to the channel region 208. In some embodiments, a first thinning, which may include plasma etch, is performed first to reduce the thickness of the substrate 201, and a last etch operation uses a non-plasma etch to expose the channel region 208 at the second surface 211 of the substrate 201. The non-plasma etch avoids plasma induced damage (PID) with residual charge at the channel region 208 of the FET 209.

Figure 6D:
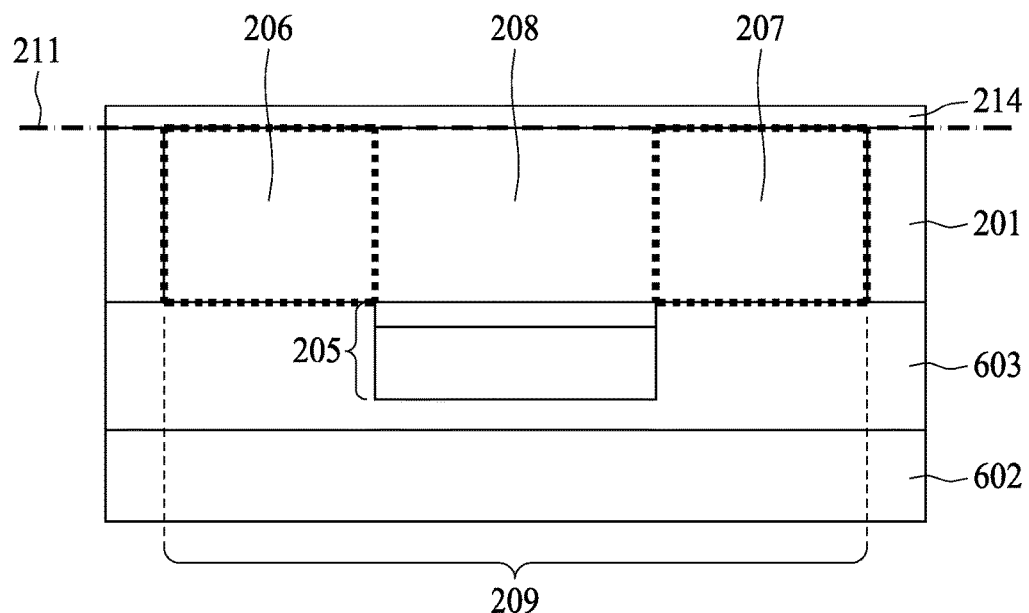
Figure 6E:
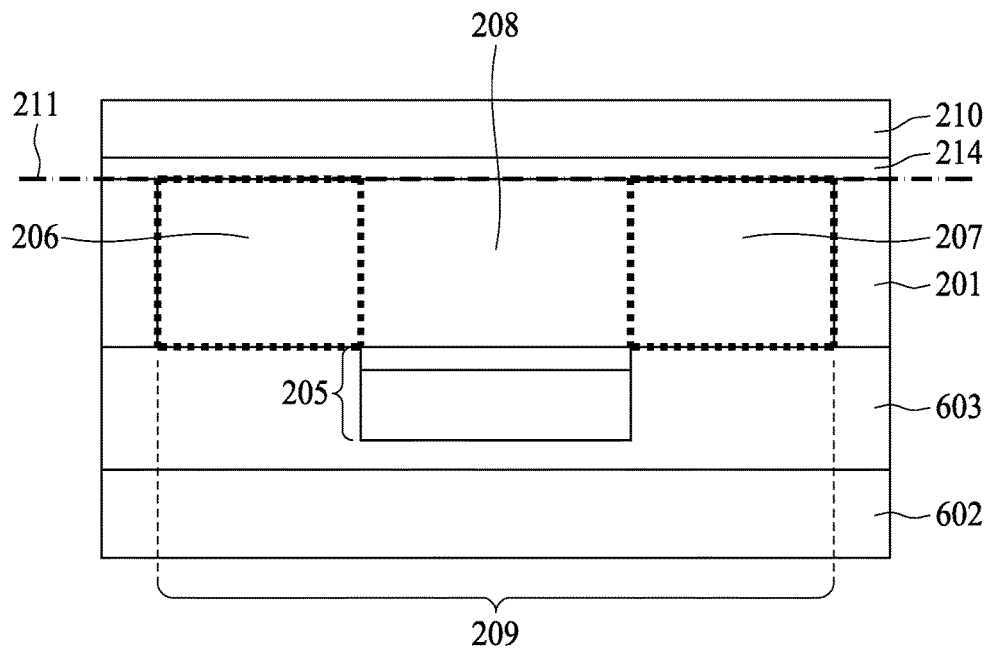
Figure 6F:
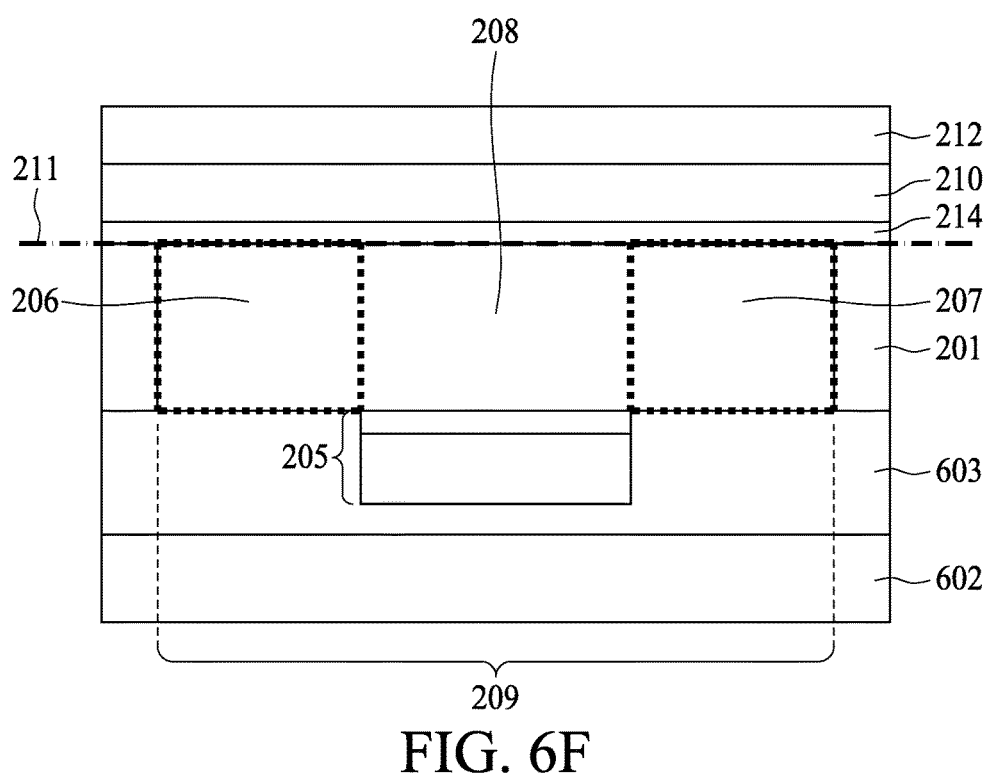
Figure 6G:
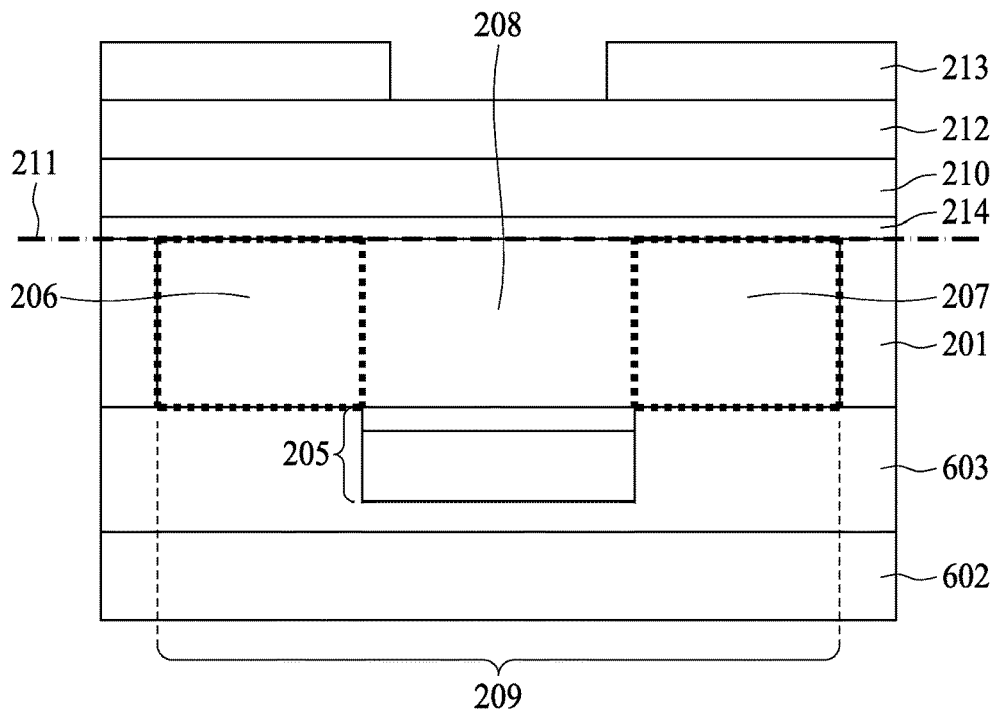
Figure 6H:
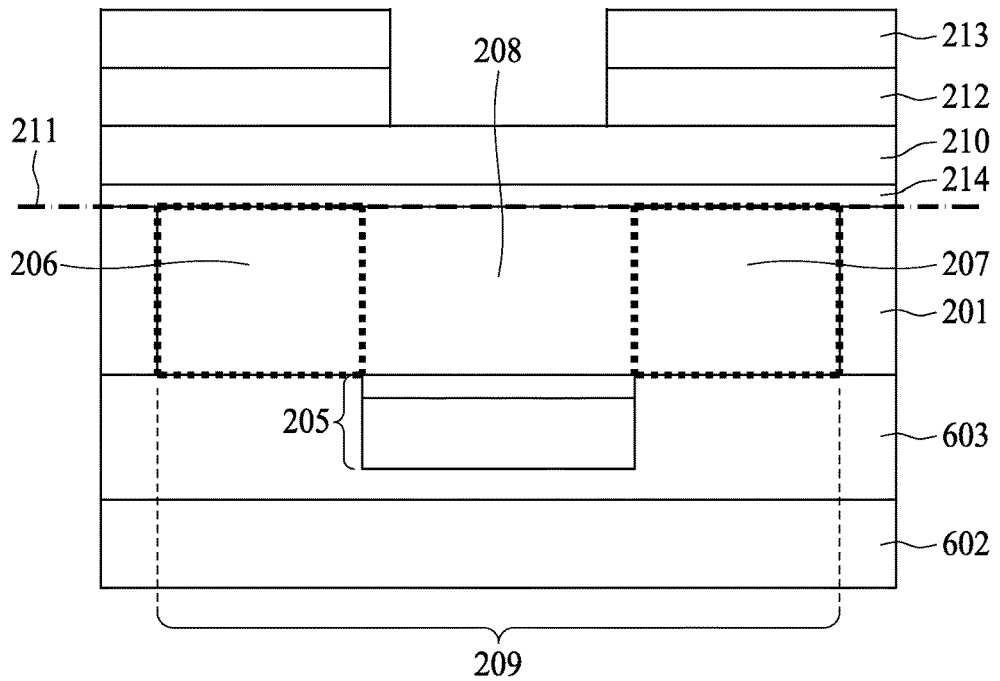
Figure 6I:
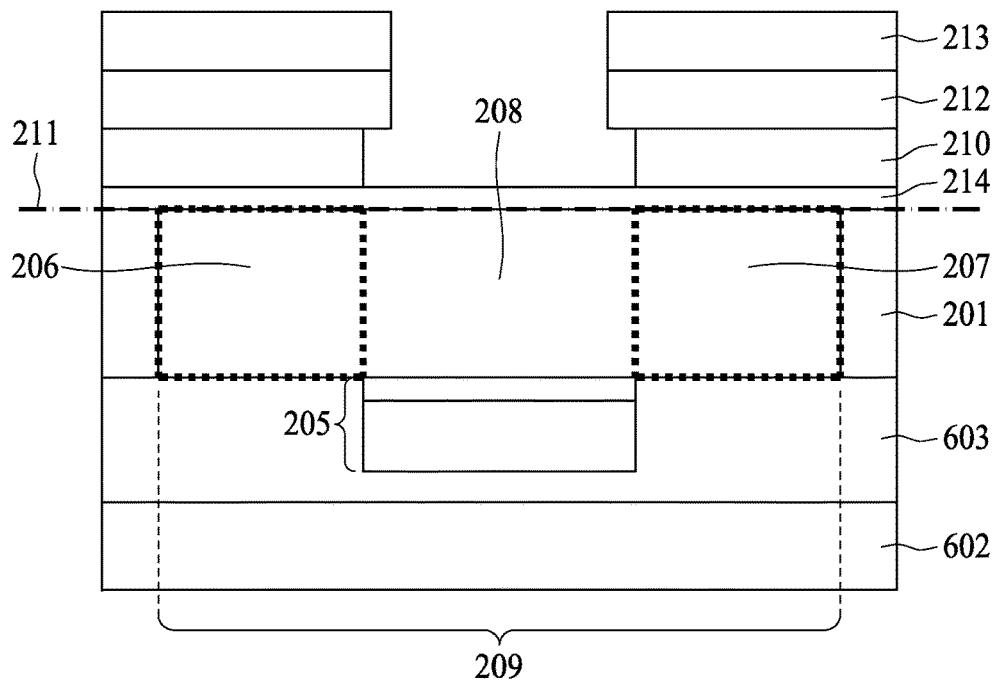
Figure 6J:
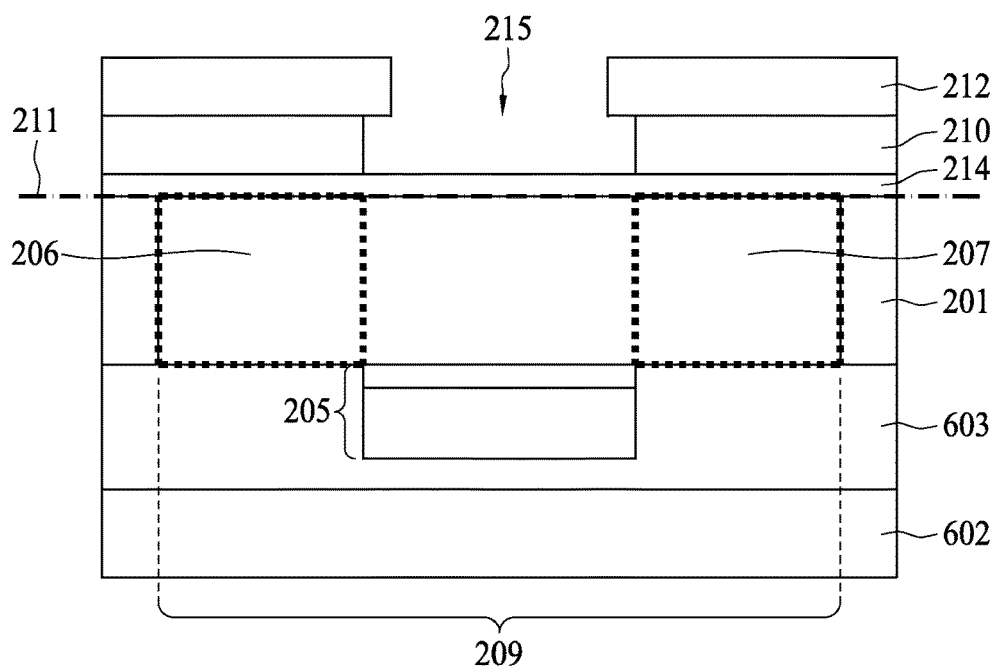

Referring to FIG. 6D, a sensing film 214 is formed over the second surface 211 of the substrate 201 opposite to the first surface 203. In some embodiments, the sensing film is selected from the group comprising $Si_3N_4$, $Al_2O_3$, $TiO_2$, $HfO_2$, $Ta_2O_5$, $SnO_2$ and combinations thereof. In FIG. 6E, a first layer 210 is formed over the sensing film 214. In FIG. 6F, a second layer 212 is formed over the first layer 210. In FIG. 6G, a photoresist 213 is formed and patterned over the second layer 212. In FIG. 6H, a portion of the second layer 212 not protected by the photoresist 213 is removed. In FIG. 6I, a portion of the first layer 210 is removed. In FIG. 6J, the photoresist 213 is removed and a well 215 is formed over the sensing film 214 and cuts off the first layer 210 and the second layer 212. In some embodiments, a third layer can be formed over the semiconductor structure shown in FIG. 6J. The semiconductor structure comprising the third layer is similar to the semiconductor structure shown in FIG. 5I.

In some embodiments, a semiconductor structure comprises a substrate, a gate structure over a first surface of the substrate, and a source region and a drain region in the substrate adjacent to the gate structure. The semiconductor structure further comprises a channel region interposing the source and drain regions and underlying the gate structure. The semiconductor structure further comprises a first layer over a second surface of the substrate opposite to the first surface, and a second layer over the first layer. The semiconductor structure further comprises a sensing film over the channel region and at least a portion of the first and second layers, and a well over the sensing film and cutting off the first layer and the second layer.

In some embodiments, the first layer is one of a nitride layer and an oxide layer. In some embodiments, the second layer is one of a nitride layer and an oxide layer. In some embodiments, the first and second layers are of different materials. In some embodiments, the semiconductor structure further comprises a third layer over the second layer. In some embodiments, the third layer is one of a nitride layer and an oxide layer. In some embodiments, the material of the third layer is the same as that of the first layer. In some embodiments, the thickness of the third layer is different from that of the first layer. In some embodiments, the sensing film comprises a material with a dielectric constant ranging from 5 to 100. In some embodiments, the substrate is a silicon-on-insulator (SOI) substrate.

In some embodiments, a semiconductor structure comprises a FET device on a substrate, wherein the FET device includes a gate structure formed over a first surface of the substrate and a channel region in the substrate below the gate structure. In some embodiments, the first surface of the substrate is attached to a carrier substrate and the channel region is away from a second surface of the substrate. In some embodiments, a sensing film is formed over the channel region on the second surface of the substrate opposite to the first surface. In some embodiments, a first layer is formed over the sensing film and a second layer is formed over the first layer. In some embodiments, a well is formed over the sensing film and cutting off the first layer and the second layer.

In some embodiments, the semiconductor structure further comprises a third layer over the second layer. In some embodiments, relative to the first layer, the second layer has a protrusion extended inwardly toward the center of the well. In some embodiments, the well is defined by the openings in the first, second and third layers. In some embodiments, the lateral widths of the first, second and third layer are different. In some embodiments, the lateral width of the first layer is greater than the widths of the second and third layers.

In some embodiments, a method for forming a semiconductor structure comprises forming a substrate, forming a gate structure over a first surface of the substrate, and forming a source region and a drain region in the substrate adjacent to the gate structure. The method further comprises forming a channel region interposing the source and drain regions and underlying the gate structure. The method further comprises forming a first layer over a second surface of the substrate opposite to the first surface and forming a second layer over the first layer. The method further comprises forming a sensing film over the channel region and over at least a portion of the first and second layers, and forming a well over the sensing film and cutting off the first layer and the second layer.

In some embodiments, the method further comprises forming a third layer over the second layer. In some embodiments, the etching selectivity of the second layer and that of the third layer are different. In some embodiments, forming the well over the channel region and cutting off the first layer and the second layer further comprises removing a portion of the first layer and the second layer by etching.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor structure, comprising:
a substrate;
a gate structure over a first surface of the substrate;
a source region and a drain region in the substrate adjacent to the gate structure;
a channel region interposing the source and drain regions and underlying the gate structure;
a first layer over the second surface of the substrate opposite to the first surface, the first layer having a first opening of a first width over the channel region;
a second layer over the first layer, the second layer having a second opening of a second width over the channel region;
a third layer over the second layer, the third layer having a third opening of a third width over the channel region;
the first opening, the second opening, and the third opening form a contiguous opening sidewall; and
a sensing film over the channel region and the contiguous opening sidewall; and
wherein the first width of the first opening is greater than the second width of the second opening, and the third width of the third opening is greater than the second width of the second opening.

2. The semiconductor structure of claim 1, wherein the first layer is one of a nitride layer and an oxide layer.

3. The semiconductor structure of claim 1, wherein the second layer is one of a nitride layer and an oxide layer.

4. The semiconductor structure of claim 1, wherein the first layer and the second layer are of different materials.

5. The semiconductor structure of claim 1, wherein the first opening exposes only the channel region interposing the source and drain regions and underlying the gate structure.

6. The semiconductor structure of claim 1, wherein the third layer is one of a nitride layer and an oxide layer.

7. The semiconductor structure of claim 1, wherein a material of the third layer is the same as that of the first layer.

8. The semiconductor structure of claim 1, wherein a thickness of the third layer is different from that of the first layer.

9. The semiconductor structure of claim 1, wherein the sensing film comprises a material with a dielectric constant ranging from about 5 to about 100.

10. The semiconductor structure of claim 1, wherein a thickness of the first layer is thinner than a thickness of the second layer.

11. The semiconductor structure of claim 1, wherein a thickness of the third layer is thicker than a thickness of the first layer or the second layer.

12. A semiconductor structure, comprising:
an FET device on a substrate, wherein the FET device includes:
a gate structure formed over a portion of a first surface of the substrate; and
a channel region in the substrate below the gate structure and away from a second surface of the substrate, the second surface being opposite to the first surface;
a first layer over the second surface of the substrate, the first layer having a first opening of a first width over the channel region;
a second layer over the first layer, the second layer having a second opening of a second width over the channel region;
a third layer over the second layer, the third layer having a third opening of a third width over the channel region;
the first opening, the second opening, and the third opening form a contiguous opening sidewall; and
a sensing film over the channel region and the contiguous opening sidewall,
wherein the third width of the third opening is greater than the second width of the second opening, and the first width of the first opening is greater than the second width of the second opening.

13. The semiconductor structure of claim 12, wherein the first opening exposes only the channel region of the FET device.

14. The semiconductor structure of claim 12, wherein a thickness of the first layer is thinner than a thickness of the second layer.

15. The semiconductor structure of claim 12, wherein a thickness of the third layer is thicker than a thickness of the first layer or the second layer.

16. A semiconductor structure, comprising:
forming a substrate;
forming a gate structure over a first surface of the substrate;
forming a source region and a drain region in the substrate adjacent to the gate structure;
forming a channel region interposing the source and drain regions and underlying the gate structure;
forming a first layer over the second surface of the substrate opposite to the first surface, the first layer having a first opening of a first width over the channel region;
forming a second layer over the first layer, the second layer having a second opening of a second width over the channel region;
forming a third layer over the second layer, the third layer having a third opening of a third width over the channel region;
the first opening, the second opening, and the third opening form a contiguous opening sidewall; and
forming a sensing film over the channel region and at least a portion of the first layer, the second layer, and the third layer; and
wherein the third width of the third opening is greater than the second width of the second opening, and the first width of the first opening is greater than the second width of the second opening.

17. The method of claim 16, wherein an etching selectivity of the second layer and that of the third layer are different.

18. The method of claim 16, wherein forming the well over the sensing film further comprises removing a portion of the first layer and the second layer by etching the first opening is formed by etching to remove a portion of the first layer, and the second opening is formed by etching to remove a portion of the second layer.

* * * * *